(12) United States Patent  
Lenaerts et al.

(10) Patent No.: US 8,487,002 B2  
(45) Date of Patent: Jul. 16, 2013

(54) CONTROLLED-RELEASE COMPOSITIONS

(75) Inventors: Vincent Lenaerts, Slough (GB); Patricia Laure Ouadji-Njiki, Montreal (CA); Johnatan Bacon, Montreal (CA); Rachid Ouzerourou, Montreal (CA); Sonia Gervais, Laval (CA); Miloud Rahmouni, Pierrefonds (CA); Damon Smith, Saint-Laurent (CA)

(73) Assignees: Paladin Labs Inc., Montreal (Quebec) (CA); Paladin Labs (Barbados) Inc., Hastings, Christ Church (BB); Paladin Labs Europe Limited, Dublin (IE)

( * ) Notice: Subject to any disclaimer, the term of this patent is extended or adjusted under 35 U.S.C. 154(b) by 2015 days.

(21) Appl. No.: 11/111,996

(22) Filed: Apr. 22, 2005

(65) Prior Publication Data

US 2006/0240107 A1  Oct. 26, 2006  
US 2010/0151022 A9  Jun. 17, 2010

Related U.S. Application Data

(63) Continuation of application No. PCT/CA03/01637, filed on Oct. 27, 2003.

(60) Provisional application No. 60/509,062, filed on Oct. 25, 2002, provisional application No. 60/510,000, filed on Oct. 10, 2003.

(51) Int. Cl.  
*A01N 37/30* (2006.01)  
*A61K 31/205* (2006.01)

(52) U.S. Cl.  
USPC .......................................................... 514/555

(58) Field of Classification Search  
USPC .......................................................... 514/555  
See application file for complete search history.

(56) References Cited

U.S. PATENT DOCUMENTS

| | | | |
|---|---|---|---|
| 2,987,445 A | 6/1961 | Levesque | |
| 3,087,860 A | 4/1963 | Endicott et al. | |
| 3,336,200 A | 8/1967 | Krause et al. | |
| 3,381,009 A | 4/1968 | Palazzo et al. | |
| 3,652,589 A | 3/1972 | Flick et al. | |

(Continued)

FOREIGN PATENT DOCUMENTS

| CA | 970688 | 7/1975 |
|---|---|---|
| CA | 2140032 | 2/1994 |

(Continued)

OTHER PUBLICATIONS

Adler, L. et al., "A Comparison of Once-Daily Tramadol with Normal Release Tramadol in the Treatment of Pain in Osteoarthritis," The Journal of Rheumatology 2002, vol. 29, No. 10, pp. 2196-2199.

(Continued)

*Primary Examiner* — Benjamin Packard  
(74) *Attorney, Agent, or Firm* — Goodwin Procter LLP

(57) ABSTRACT

A solid dosage formulation having a core with a pharmacological agent dispersed in a first controlled-release matrix from which release of the agent is relatively slow; and a coat formed over the core and having the agent dispersed in a second controlled-release matrix from which release of the agent is relatively fast. The first matrix can be a cross-linked high amylose starch and the second matrix can be a mixture of polyvinyl acetate and polyvinylpyrrolidone.

23 Claims, 6 Drawing Sheets

U.S. PATENT DOCUMENTS

| | | | |
|---|---|---|---|
| 4,131,675 A | 12/1978 | Silvestrini | |
| 4,820,522 A | 4/1989 | Radebaugh et al. | |
| 4,906,632 A | 3/1990 | Silvestrini et al. | |
| 4,938,968 A * | 7/1990 | Mehta | 424/495 |
| 4,968,509 A | 11/1990 | Radebaugh et al. | |
| 5,004,613 A | 4/1991 | Radebaugh et al. | |
| 5,133,974 A | 7/1992 | Paradissis et al. | |
| 5,273,760 A | 12/1993 | Oshlack et al. | |
| 5,286,493 A | 2/1994 | Oshlack et al. | |
| 5,336,691 A | 8/1994 | Raffa et al. | |
| 5,407,686 A | 4/1995 | Patel et al. | |
| 5,414,129 A | 5/1995 | Cherkez et al. | |
| 5,427,799 A | 6/1995 | Valentine et al. | |
| 5,456,921 A * | 10/1995 | Mateescu et al. | 424/465 |
| 5,478,577 A | 12/1995 | Sackler et al. | |
| 5,520,931 A | 5/1996 | Persson et al. | |
| 5,560,331 A | 10/1996 | Komatsu et al. | |
| 5,562,924 A | 10/1996 | Perrier et al. | |
| 5,580,578 A | 12/1996 | Oshlack et al. | |
| 5,591,452 A | 1/1997 | Miller et al. | |
| 5,595,762 A | 1/1997 | Derrieu et al. | |
| 5,601,842 A | 2/1997 | Bartholomaeus et al. | |
| 5,603,956 A | 2/1997 | Mateescu et al. | |
| 5,616,343 A | 4/1997 | Cartilier et al. | |
| 5,639,476 A | 6/1997 | Oshlack et al. | |
| 5,663,279 A | 9/1997 | Kuiper et al. | |
| 5,672,360 A | 9/1997 | Sackler et al. | |
| 5,672,755 A | 9/1997 | Lerman et al. | |
| 5,681,585 A | 10/1997 | Oshlack et al. | |
| 5,773,031 A | 6/1998 | Shah et al. | |
| 5,776,492 A | 7/1998 | Betzing et al. | |
| 5,780,057 A | 7/1998 | Conte et al. | |
| 5,807,575 A | 9/1998 | Dumoulin et al. | |
| 5,814,338 A | 9/1998 | Veronesi et al. | |
| 5,843,480 A | 12/1998 | Miller et al. | |
| 5,849,240 A | 12/1998 | Miller et al. | |
| 5,874,620 A | 2/1999 | Lerman et al. | |
| 5,877,351 A | 3/1999 | Anderson | |
| 5,879,705 A | 3/1999 | Heafield et al. | |
| 5,879,707 A | 3/1999 | Cartilier et al. | |
| 5,885,615 A | 3/1999 | Chouinard et al. | |
| 5,891,471 A | 4/1999 | Miller et al. | |
| 5,958,459 A | 9/1999 | Chasin et al. | |
| 5,965,163 A | 10/1999 | Miller et al. | |
| 5,968,551 A | 10/1999 | Oshlack et al. | |
| 5,981,592 A | 11/1999 | Wechter et al. | |
| 6,103,261 A | 8/2000 | Chasin et al. | |
| 6,129,205 A | 10/2000 | Ergenbright et al. | |
| 6,129,933 A | 10/2000 | Oshlack et al. | |
| 6,143,322 A | 11/2000 | Sackler et al. | |
| 6,143,325 A | 11/2000 | Dennis et al. | |
| 6,143,328 A | 11/2000 | Heafield et al. | |
| 6,143,353 A | 11/2000 | Oshlack et al. | |
| 6,156,342 A | 12/2000 | Sriwongjanya et al. | |
| 6,156,343 A | 12/2000 | Morita et al. | |
| 6,162,467 A | 12/2000 | Miller et al. | |
| 6,190,591 B1 | 2/2001 | van Lengerich | |
| 6,210,714 B1 | 4/2001 | Oshlack et al. | |
| 6,211,229 B1 | 4/2001 | Kavey | |
| 6,214,331 B1 | 4/2001 | Vanderhoff et al. | |
| 6,228,875 B1 | 5/2001 | Tsai et al. | |
| 6,238,698 B1 | 5/2001 | Cremer et al. | |
| 6,245,357 B1 | 6/2001 | Edgren et al. | |
| 6,245,387 B1 | 6/2001 | Hayden | |
| 6,248,363 B1 | 6/2001 | Patel et al. | |
| 6,254,881 B1 | 7/2001 | McNally et al. | |
| 6,254,887 B1 | 7/2001 | Miller et al. | |
| 6,277,887 B1 | 8/2001 | Young | |
| 6,284,273 B1 | 9/2001 | Lenaerts et al. | |
| 6,294,195 B1 | 9/2001 | Oshlack et al. | |
| 6,306,438 B1 | 10/2001 | Oshlack et al. | |
| 6,316,031 B1 | 11/2001 | Oshlack et al. | |
| 6,326,027 B1 | 12/2001 | Miller et al. | |
| 6,326,404 B1 | 12/2001 | Koegel et al. | |
| 6,339,105 B1 | 1/2002 | Kamin et al. | |
| 6,372,255 B1 | 4/2002 | Saslawski et al. | |
| 6,387,404 B2 | 5/2002 | Oshlack et al. | |
| 6,399,096 B1 | 6/2002 | Miller et al. | |
| 6,419,957 B1 | 7/2002 | Lenaerts et al. | |
| 6,451,350 B1 | 9/2002 | Bartholomaeus et al. | |
| 6,569,463 B2 | 5/2003 | Patel et al. | |
| 6,572,885 B2 | 6/2003 | Oshlack et al. | |
| 6,576,260 B2 | 6/2003 | Bartholomaeus et al. | |
| 6,586,006 B2 | 7/2003 | Roser et al. | |
| 6,593,373 B2 | 7/2003 | Koegel et al. | |
| 6,607,748 B1 | 8/2003 | Lenaerts et al. | |
| 6,632,640 B1 | 10/2003 | Lee et al. | |
| 6,635,279 B2 | 10/2003 | Kolter et al. | |
| 6,645,537 B2 | 11/2003 | Sweeney et al. | |
| 6,659,373 B1 | 12/2003 | Heren et al. | |
| 6,660,774 B2 | 12/2003 | Christoph et al. | |
| 6,685,964 B1 | 2/2004 | Bartholomaeus et al. | |
| 6,723,343 B2 | 4/2004 | Kugelmann et al. | |
| 6,733,783 B2 | 5/2004 | Oshlack et al. | |
| 6,743,442 B2 | 6/2004 | Oshlack et al. | |
| 6,806,293 B1 | 10/2004 | Zamir et al. | |
| 6,806,294 B2 | 10/2004 | Wimmer et al. | |
| 6,863,901 B2 | 3/2005 | Hirsh et al. | |
| 6,923,988 B2 | 8/2005 | Patel et al. | |
| 6,962,717 B1 | 11/2005 | Huber et al. | |
| 6,968,551 B2 | 11/2005 | Hediger et al. | |
| 7,074,430 B2 | 7/2006 | Miller et al. | |
| RE39,221 E | 8/2006 | Raffa et al. | |
| 7,083,807 B2 | 8/2006 | Fanara et al. | |
| 7,413,749 B2 | 8/2008 | Wright et al. | |
| 2001/0019725 A1 | 9/2001 | Miller et al. | |
| 2001/0036477 A1 | 11/2001 | Miller et al. | |
| 2001/0038852 A1 | 11/2001 | Kolter et al. | |
| 2002/0008133 A1 | 1/2002 | Imasaki et al. | |
| 2002/0012701 A1 | 1/2002 | Kolter et al. | |
| 2002/0032239 A1 | 3/2002 | Koegel et al. | |
| 2002/0044966 A1 | 4/2002 | Bartholomaeus et al. | |
| 2002/0055544 A1 | 5/2002 | Kamin et al. | |
| 2002/0106408 A1 | 8/2002 | Bacon et al. | |
| 2002/0165246 A1 | 11/2002 | Holman | |
| 2002/0176888 A1 | 11/2002 | Bartholomaeus et al. | |
| 2003/0021846 A1 | 1/2003 | Kolter et al. | |
| 2003/0035835 A1 | 2/2003 | Bartholomaeus et al. | |
| 2003/0044464 A1 | 3/2003 | Ziegler et al. | |
| 2003/0054032 A1 | 3/2003 | Oshlack et al. | |
| 2003/0069314 A1 | 4/2003 | Christoph et al. | |
| 2003/0092724 A1 | 5/2003 | Kao et al. | |
| 2003/0104061 A1 | 6/2003 | Bartholomaeus et al. | |
| 2003/0143270 A1 | 7/2003 | Deboeck et al. | |
| 2003/0148992 A1 | 8/2003 | Block et al. | |
| 2003/0152627 A1 | 8/2003 | Beckert et al. | |
| 2003/0158242 A1 | 8/2003 | Kugelmann | |
| 2003/0180362 A1 | 9/2003 | Park et al. | |
| 2004/0131671 A1 | 7/2004 | Zhang et al. | |
| 2004/0136924 A1 * | 7/2004 | Boyd et al. | 424/48 |
| 2004/0202716 A1 | 10/2004 | Chan et al. | |
| 2004/0259956 A1 | 12/2004 | Wright et al. | |
| 2005/0003002 A1 | 1/2005 | Ziegler et al. | |
| 2005/0157382 A1 | 7/2005 | Kafka et al. | |
| 2005/0256131 A1 | 11/2005 | Coester | |
| 2005/0276852 A1 | 12/2005 | Davis et al. | |
| 2006/0111307 A1 | 5/2006 | Robbins | |
| 2006/0172006 A1 | 8/2006 | Lenaerts et al. | |
| 2006/0269603 A1 | 11/2006 | Brown Miller et al. | |
| 2007/0003618 A1 | 1/2007 | Lenaerts et al. | |
| 2007/0048376 A1 | 3/2007 | Baichwal et al. | |
| 2007/0128269 A1 | 6/2007 | Gervais et al. | |
| 2007/0128275 A1 | 6/2007 | Gervais et al. | |
| 2007/0237816 A1 | 10/2007 | Finkelstein | |
| 2009/0047345 A9 | 2/2009 | Lenaerts et al. | |

FOREIGN PATENT DOCUMENTS

| | | |
|---|---|---|
| CA | 2280534 | 8/1998 |
| CA | 2321461 | 9/1999 |
| CA | 2295469 | 7/2000 |
| CA | 2414349 | 1/2002 |
| CA | 2433668 | 6/2002 |
| CA | 2466032 | 5/2003 |
| CA | 2503155 | 5/2004 |
| CA | 2503361 | 5/2004 |
| CA | 2489855 | 4/2005 |
| CL | 172000 | 10/2000 |

| | | |
|---|---|---|
| DE | 4315525 | 11/1994 |
| DE | 4329794 | 3/1995 |
| DE | 19530575 | 2/1997 |
| DE | 19901683 | 7/2000 |
| DE | 19901687 | 7/2000 |
| DE | 19940740.1 | 3/2001 |
| DE | 19940944.7 | 3/2001 |
| DE | 10023699.5 | 4/2001 |
| DE | 19947747 | 4/2001 |
| DE | 19901686 | 6/2006 |
| EP | 0 566 709 | 10/1993 |
| EP | 0 624 366 | 11/1994 |
| EP | 0624366 | 11/1994 |
| EP | 0624366 B1 * | 11/1994 |
| EP | 0636370 | 2/1995 |
| EP | 0 642 788 | 3/1995 |
| EP | 0654263 | 5/1995 |
| EP | 0699436 | 3/1996 |
| EP | 0 729 751 | 9/1996 |
| EP | 0759296 | 2/1997 |
| EP | 0 864 325 | 9/1998 |
| EP | 1020183 | 7/2000 |
| EP | 1020185 | 7/2000 |
| EP | 1020186 | 7/2000 |
| EP | 1 138 320 | 10/2001 |
| EP | 1 190 712 | 3/2002 |
| EP | 1207866 | 5/2002 |
| EP | 1207867 | 5/2002 |
| EP | 1207868 | 5/2002 |
| EP | 1217998 | 7/2002 |
| EP | 1 468 679 | 10/2004 |
| EP | 1 527 775 | 5/2005 |
| EP | 1627633 | 2/2006 |
| GB | 2284760 | 6/1995 |
| NZ | 333401 | 10/1999 |
| WO | WO-94/02121 | 2/1994 |
| WO | WO-98/40053 | 9/1998 |
| WO | WO-99/01111 | 1/1999 |
| WO | WO-00/25769 | 5/2000 |
| WO | WO-00/32558 | 6/2000 |
| WO | WO-00/41681 | 7/2000 |
| WO | WO-01/15667 | 3/2001 |
| WO | WO-01/15681 | 3/2001 |
| WO | WO-01/15682 | 3/2001 |
| WO | WO-01/15683 | 3/2001 |
| WO | WO-01/24783 | 4/2001 |
| WO | WO-01/45676 | 6/2001 |
| WO | WO-02/02084 A1 | 1/2002 |
| WO | WO-0202084 | 1/2002 |
| WO | WO-02/60415 | 8/2002 |
| WO | WO-0266026 A2 | 8/2002 |
| WO | WO-03037296 | 5/2003 |
| WO | WO-03/80031 | 10/2003 |
| WO | WO-2004003722 | 1/2004 |
| WO | WO-2004038428 | 5/2004 |
| WO | WO-04/80447 | 9/2004 |
| WO | WO-03/72025 | 1/2007 |

OTHER PUBLICATIONS

Bodalia et al., "A Comparison of the Pharmacokinetics, Clinical Efficacy, and Tolerability of Once-Daily Tramadol Tablets with Normal Release Tramadol Capsules," Journal of Pain and Symptom Management, vol. 25, No. 2, pp. 142-149 (2003).
Boureau, "Tramadol in Post-Herpetic Neuralgia: A Randomized, Double-Blind, Placebo-Controlled Trial," PAIN, Elsevier Sci Pub. 2003, vol. 104 (1/2):323-331.
Brooks et al., "Trazodone—A Comparison of Single Night-time and Divided Daily Dosage Regimens," Psychopharmacology 84:1-4 (1984).
Desmeules, "The tramadol option," European Journal of Pain, 4, Suppl. A:15-21 (2000).
Fabre, "Trazodone Dosing Regimen: Experience with Single Daily Administration," J. Clin. Psychiatry 51:9 (suppl.), pp. 23-26 (1990).
Fleischmann, "Tramadol for the treatment of joint pain associated with osteoarthritis: a randomized, double-blind, placebo-controlled trial," Current Therapeutic Research 62(2):113-128 (2001).
Haria et al., "Trazodone: A Review of its Pharmacology, Therapeutic Use in Depression and Therapeutic Potential in Other Disorders," Drugs & Aging 4(4):331-355 (1994).
International Search Report for International Patent Application No. PCT/CA03/01637, dated Apr. 27, 2004.
International Search Report for International Patent Application No. PCT/CA03/01638, dated Apr. 27, 2004.
Kasper et al., "A Comparative, Randomised, Double-Blind Study of Trazodone Prolonged-Release and Paroxetine in the Treatment of Patients with Major Depressive Disorder," Current Med. Res. & Opinion vol. 21 No. 8, pp. 1139-1146 (2005).
Klaschik, "Office-oriented pain therapy in cancer patients—Adequate alleviation of pain with the appropriate medication," Klinikarzt 31(9):250-256 (2002). (English abstract provided on p. 256).
Mateescu, "Use of Crosslinked Amylose for the Quantitative Determination of $\alpha$- and $\beta$- Amylase," Lab. Enzymol., Inst. Sci. Biol., Bucharest, Rom., Biochimie 60(5), 535-7 (1978) (English Abstract provided).
Mendelson, "A Review of the Evidence for the Efficacy and Safety of Trazodone in Insomnia," J. Clin. Psychiatry 66:4, pp. 469-476 (2005).
Moon et al., "Efficacy and Tolerability of Controlled-Release Trazodone in Depression: A Large Multi-Centre Study in General Practice," Current Med. Res. And Opinion vol. 12, No. 3, pp. 160-168 (1990).
Partial European Search Report for EP 04 02 4164, Aug. 9, 2006.
Ruoff, "Slowing the initial titration rate of tramadol improves tolerability," Pharmacotherapy 19(1):88-93 (1999-01).
Saletu-Zyhlarz et al., "Confirmation of the Neurophysiologically Predicted Therapeutic Effects of Trazodone on Its Target Symptoms Depression, Anxiety and Insomnia by Postmarketing Clinical Studies with a Controlled-Release Formulation in Depressed Outpatients," Neuropsychobiology 2003; 48:194-208.
Search Report and Written Opinion for Intl. Application PCT/CA2006/001483, Jun. 4, 2007.
Search Report and Written Opinion for Intl. Application PCT/CA2006/001484, Jun. 8, 2007.
Stamer, "Impact of CYP2D6 genotype on postoperative tramadol analgesia," PAIN, 105(1-2):231-238 (2003).
Visavarungroj, N. et al., "Crosslinked Starch as a Disintegrating Agent," International Journal of Pharmaceutics 1990, vol. 62, No. 2/3, pp. 125-131.
De Jong (1997) "Comment on the hypoalgesic effect of tramadol in relation to CYP2D6,'" Pain Dig. 7: 245.
Kogel et al., "Involvement of Metabolites in the Analgesic Action of Tramadol," Proc. 9th World Congress on Pain, Vienna, Austria, Aug. 22-27, 1999, pp. 523.
Roth (1998) "Efficacy and Safety of Tramadol HCL in Breakthrough Musculoskeletal Pain Attributed to Osteoarthritis," J. Rheumatol. 25:1358-63.
Ruoff (1999) "Strategies to Control Chronic Musculoskeletal Pain: A Guide to Drug Therapy," Consultant 39: 2773-81.
Wilder-Smith et al. (2001) "Treatment of Severe Pain from Osteoarthritis with Slow-Release Tramadol or Dihydrocodeine in Combination with NSAID's: A Randomized Study Comparing Analgesia, Antinociception and Gastrointestinal Effects," Pain 91: 23-31.
Excerpt from "Controlled Drug Delivery. Fundamentals and Applications," Second Edition, Revised and Expanded, Joseph R. Robinson, et al., Editors (1987) (68 pages).
Excerpt from "Handbook of Pharmaceutical Controlled Release Technology," Donald L. Wise, Executive Editor (2000) (80 pages).
Gennaro R. Alfonso, Remington Farmacia, 19th Edition, Panamericana, Spain. 1988, pp. 2470, 2535 (in Spanish) and an English translation.
Labopharm, Inc. Press Release dated Feb. 2, 2010 relating to FDA approval of OLEPTRO® (4 pages).
Nies and Spielberg, Goodman & Gilman. Las Bases Farmacologicas de la Terapeutica. Novena Edicion. vol. I. McGraw-Hill. Interamericana. Mexico. 1996, pp. 47, 58(in Spanish) and an English translation.
Opposition statement against Ecuadorian Application No. SP 08-8239 by Asociacion de Laboratorios Farmaceuticos (ALAFAR) (in Spanish) and an English translation, 2008.

Opposition statement against Ecuadorian Application No. SP 08-8240 by Asociacion de Laboratorios Farmaceuticos (ALAFAR) (in Spanish) and an English translation, 2008.

Opposition statement against Chilean Application No. 2186-2003 by La Asociacion Industrial De Laboratorios Farmaceuticos A.G. (in Spanish) and its English translation, 2003.

Opposition statement against Chilean Application No. 2187-2003 by La Asociacion Idustrial De Laboratorios Farmaceuticos A.G. (in Spanish) and its English translation, 2003.

Opposition statement against Chilean Application No. 2187-2003 by Laboratorios Recalcine S.A. (in Spanish) and its English translation, 2003.

Opposition statement against Chilean Application No. 600-2007 by Asociacion Industrial de Laboratorios Farmaceuticos A.G. (in Spanish) and an English translation, 2007.

Opposition statement against Chilean Application No. 605-2007 by Asociacion Industrial de Laboratorios Farmaceuticos AG (in Spanish) and an English translation, 2007.

Opposition statement against Chilean Application No. 605-2007 by Laboratorios Recalcine S.A. (in Spanish) and an English translation, 2007.

* cited by examiner

CONTROLLED-RELEASE COMPOSITIONS

CROSS-REFERENCE TO RELATED APPLICATIONS

This application is a continuation of International (PCT) Patent Application Serial No. PCT/CA2003/001637, filed Oct. 27, 2003, which claims priority to and the benefit under 35 U.S.C. §119(e) of U.S. Provisional Application Ser. No. 60/510,000, filed Oct. 10, 2003, and U.S. Provisional Application Ser. No. 60/509,062, filed Oct. 25, 2002.

FIELD OF THE INVENTION

This invention relates to a solid dosage formulation in which an active ingredient is released over a sustained period.

BACKGROUND OF THE INVENTION

An important factor influencing the rate of absorption of an active agent administered as a tablet or other solid dosage formulation, and thus the efficacy and safety of the formulation, is the rate of dissolution of the dosage form in the body fluids of a human or animal The ability of components of the formulation to influence the rate of release of the active agent(s) thus constitutes the basis for the so-called controlled-release, extended-release, sustained-release or prolonged-action pharmaceutical preparations that are designed to produce slow, uniform release and absorption of the active agent over a period of hours, days, weeks, or months. Advantages of controlled-release formulations include a reduction in the required frequency of administration of the drug as compared to immediate-release dosage forms, often resulting in improved patient compliance; maintenance of a relatively stable concentration of the drug in the body leading to a sustained therapeutic effect over a set period of time; and decreased incidence and intensity of undesired side effects of the active agent resulting from a reduction of the high plasma concentrations that often occur after administration of immediate-release dosage forms Many materials have been proposed and developed as matrices for controlled release of active agents, i.e. drugs, pro-drugs, etc. These include polymeric materials such as polyvinyl chloride, polyethylene amides, ethyl cellulose, silicone and poly (hydroxymethyl methacrylate). See, for example, U.S. Pat. No. 3,087,860 to Endicott et al.; U.S. Pat. No. 2,987,445 to Levesque et al.; Salomon et al., Pharm. Acta Helv., 55, 174-182 (1980); Korsmeyer, Diffusion Controlled Systems: Hydrogels, Chap. 2, pp 15-37 in Polymers for Controlled Drug Delivery, Ed Tarcha, CRC Press, Boca Raton, Fla. USA (1991); and Buri et al., Pharm. Acta Helv. 55, 189-197(1980).

High amylose starch has also been used for controlled-release purposes, and, in particular, recent advances have been made using cross-linked high amylose starch. For example, U.S. Pat. No. 5,456,921 (Mateescu et al.), which issued Oct. 10, 1995, U.S. Pat. No. 5,616,343 (Cartilier et al.), which issued Apr. 1, 1997, U.S. Pat. No. 6,284,273 (Lenaerts et al.), which issued Sep. 4, 2001, U.S. Pat. No. 6,419,957 (Lenaerts et al.), which issued Jul. 16, 2002, and U.S. Pat. No. 6,607,748 (Lenaerts et al.), which issued Aug. 19, 2003, describe solid controlled release oral pharmaceutical dosage units in the form of tablets comprising a dry powder of a pharmaceutical product and a dry powder of cross-linked high amylose starch in which the cross-linked high amylose starch includes a mixture of about 10-60% by weight of amylopectin and about 40-90% amylose.

Further examples of controlled-release materials include Kollidon™ SR marketed by BASF (Germany), this material being a physical mixture of polyvinyl acetate (PVA) and polyvinylpyrrolidone (povidone), reportedly made up of about 80% PVA and 19% povidone, and approximately 0.8% sodium dodecylsulfate and about 0.2% silica as stabilizer. BASF Technical Information (July 2001) discloses that Kollidon™ SR can be used in the preparation of sustained release matrix dosage forms including tablets, pellets and granules, and that different technologies such as direct compression, roller compaction, wet granulation and extrusion may be employed in the manufacture of pharmaceutical formulations. A number of patent publications provide further information on PVA-povidone mixtures: U.S. Patent Publication No. 2001/0038852 (Kolter et al.) published Nov. 8, 2001; U.S. Patent Publication No. 2002/0012701 (Kolter et al.) published Jan. 31, 2002, and U.S. Patent Publication No. 2003/0021846 (Kolter et al.) published Jan. 30, 2003.

Extended and controlled release formulations relating to tramadol have been suggested, examples being described in: U.S. Patent Publication No. 2003/0143270, (Deboeck et al.) published Jul. 31, 2003; U.S. Pat. No. 6,254,887 (Miller et al.) issued Jul. 3, 2001; U.S. Patent Publication No. 2001/0036477 (Miller et al.) published Nov. 1, 2001; U.S. Pat. No. 6,326,027 (Miller et al.) issued Dec. 4, 2001, WO 03/080031 (CILAG AG et al.) published Oct. 2, 2003. Articles have been published in which comparative data between "once-daily" tramadol formulations and immediate release tramadol formulations are presented: Adler et al., "A Comparison of Once-Daily Tramadol with Normal Release Tramadol in the Treatment of Pain in Osteoarthritis," The Journal of Rheumatology (2002) 29(10): 2195-2199; and Bodalia et al., "A Comparison of the Pharmacokinetics, Clinical Efficacy, and Tolerability of Once-Daily Tramadol Tablets with Normal Release Tramadol Capsules," Journal of Pain and Symptom Management (2003) 25(2): 142-149.

Citation or identification of any reference in this specification is not intended to be construed as an admission that such reference is available as prior art to the present invention.

SUMMARY OF THE INVENTION

The present invention relates to a solid dosage formulation that provides for controlled-release of a pharmacological agent. In one embodiment, the formulation includes a core having a pharmacological agent dispersed in a first controlled-release matrix comprising cross-linked high amylose starch, from which matrix release of the agent is relatively slow. There is a coat formed over the core and the coat includes the agent dispersed in a second controlled-release matrix from which release of the agent is relatively fast.

In the context of this invention, "relatively fast" means at least twice as fast when the initial rate of release of an agent is measured under the same conditions separately for each matrix material. To make such a measurement, one makes a formulation having the agent of the core and the agent of the coat differentially labeled from each other. In the case of tramadol, for example, the tramadol of the core could be labeled with $^{15}$N and the tramadol of the coat could be labeled with $^{13}$C. There are many ways known to a skilled person for differentially labeling such a compound so that its diffusion from the formulation can be traced without significantly affecting its rate of diffusion. A skilled person could estimate such relative rates to a reasonable approximation, provided the rates are sufficiently different from each other, from the z behavior observed for release of the agent from a single formulation, e.g., from the rates at t=0, and t=12 hr of FIG. 2.

Typically, the measurement would be made under the conditions set forth in connection with FIG. 2.

In another broad embodiment, the invention is a solid dosage formulation having a core with a pharmacological agent in a first controlled-release matrix. There is a coat formed over the core having the pharmacological agent in a second controlled-release matrix. The second controlled-release matrix is a physical mixture of polyvinyl acetate and polyvinylpyrrolidone, and release of the agent from the matrix of the core is relatively slow with respect to release of the agent from the matrix of the coat. Relatively slow means no more than half as fast when the initial rate of release of an agent is measured under the same conditions separately for each matrix material, the measurement being determined as described above in connection with the determination of relatively fast.

The agent in the core and coat may, in either embodiment, be the same or different. In a preferred embodiment, the formulation includes a single agent that is tramadol.

In a preferred aspect of the invention, the coat and core comprise relative amounts of the agent such that release of the agent from the formulation is biphasic.

Preferably, the agent is soluble in water, and the first matrix is relatively hydrophilic relative to the second matrix.

Many agents are capable of forming ionic salts, and this is often the preferred form of the agent for incorporation into a formulation of the invention. Preferred agents contain at least one amino group, and these are conveniently incorporated in the form of, for example a hydrochloride salt.

Preferably, the rate of release of the agent from the coat is at least twice the rate of release of the agent from the core. Other relative rates are possible: the rate of release of the agent from the coat can be at least three times the rate of release of the agent from the core; the rate of release of the agent from the coat can be up to fifteen times the rate of release of the agent from the core; the rate of release of the agent from the coat can be up to twelve times the rate of release of the agent from the core; the rate of release of the agent from the coat can be up to ten times the rate of release of the agent from the core; the rate of release of the agent from the coat can be up to eight times the rate of release of the agent from the core; the rate of release of the agent from the coat can be up to six times the rate of release of the agent from the core; or the rate of release of the agent from the coat can be about four times the rate of release of the agent from the core. In other embodiments, biphasic release behavior is observed, and the rate of release of the agent from the coat is between three and nine times the rate of release of the agent from the core, more preferably the rate of release of the agent from the coat is between four and eight times the rate of release of the agent from the core, more preferably the rate of release of the agent from the coat is between five and seven times the rate of release of the agent from the core.

In certain embodiments, between 10% and 30% per hour of the agent is released between 0 and 2 hours when tested in vitro using a USP Type I apparatus in 50 mM phosphate, pH 6.8, and stirring between 50 and 150 rpm In certain embodiments, between 10% and 40% of the agent is released from the formulation between 0 and about 2 hours of measurement, between about 30% and 60% of the agent is released from the formulation between 2 and about 7 hours of the measurement, between about 50% and 80% of the agent is released from the formulation between 7 and about 12 hours of measurement, and between about 80% and 100% of the agent is released from the formulation after about 20 hours of measurement.

A preferred active agent of both the core and the coat is an analgesic, specifically, the active can be tramadol.

An agent of the formulation of the invention is preferred to be soluble in water at least to the extent of 1 g/L, or more than 10 g/L, or more than 100 g/L, or more than 500 g/L, or more than 1000 g/L, or more than 2000 g/L.

In certain embodiments, the formulation of the invention is generated to have the ratio of the core to the coat (w/w) between about 1 and about 0.1, or between about 0.9 and about 0.2, or between about 0.8 and about 0.2, or between about 0.7 and about 0.2, or between about 0.5 and about 0.2, or between about 0.4 and about 0.2, or about 0.35. In this context, it is the total weight of the core and the total weight of the coat that would be considered when determining the weight ratio.

In certain embodiments, the ratio of the agent in core to the agent in the coat (w/w) is between about 0.1 and about 10, or between about 0.1 and about 8, or between about 0.2 and about 7, or between about 0.3 and about 6, or between about 0.4 and about 5, or between about 0.5 and about 4, or between about 0.6 and about 3, or between about 0.6 and about 2, or between about 0.6 and about 1.5, or between about 0.6 and about 1.3, or between about 0.7 and about 1, or between about 0.7 and about 0.9 or about 0.8.

In particular embodiments of the invention, a formulation is one in which the core is between about 10% and about 90% by weight agent, or between about 20% and about 80% by weight agent, or between about 30% and about 70% by weight agent, or between about 40% and about 60% by weight agent, or about 50% by weight agent.

In particular embodiments, a formulation of the invention is one in which the coat is between about 5% and about 90% by weight agent, or between about 5% and about 80% by weight agent, or between about 10% and about 70% by weight agent, or between about 10% and about 60% by weight agent, or between about 15% and about 50% by weight agent, or between about 15% and about 45% by weight agent, or between about 15% and about 40% by weight agent, or between about 20% and about 35% by weight agent, or between about 20% and about 30% by weight agent.

According to certain aspects of the invention, the formulation is such that the ratio of the matrix of the coat to the agent of the coat (w/w) is between about 0.1 and about 10, or between about 0.2 and about 9, or between about 0.2 and about 8, or between about 0.3 and about 7, or between about 0.4 and about 6, or between about 0.5 and about 5, or between about 0.6 and about 4, or between about 0.7 and about 4 or between about 1 and about 4, or between about 1 and about 3 and about 1.5 and about 2.5.

According to certain aspects, the formulation is such that the ratio of the matrix of the core to the agent of the core (w/w) is between about 0.1 and about 10, or between about 0.2 and about 9, or between about 0.3 and about 7, or between about 0.4 and about 6, or between about 0.5 and about 5, or between about 0.5 and about 4, or between about 0.5 and about 3, or between about 0.6 and about 3, or between about 0.7 and about 2 or between about 0.8 and about 1.5, or between about 0.9 and about 1.5, or between about 0.9 and about 1.3, or about 1, or is about 0.55.

Preferably, the agent is a single agent soluble in water at room temperature (about 21° C.) to the extent of at least 0.5 gm per mL.

In certain aspects, each agent of the formulation contains an acid group, a base group or both an add group and a base group, and each agent is present in the form of a salt of such group. Preferably, the agent contains an ionizable group and said group is at least 90% ionized in gastric juices (0.1M HCl).

Agents of a formulation of the invention can be any one or more of the following: isonicotnic acid hydrazide, sodium salicylate, pseudoephedrine hydrochloride, pseudoephedrine sulfate, acetaminophen or diclofenac sodium, verapamil, glipizide, nifedipine, felodipine, betahistine, albuterol, acrivastine, omeprazole, misoprostol, tramadol, oxybutynin, trimebutine, ciprofloxacin, and salts thereof. In addition, the pharmaceutical agent can be an antifungal agent, such as ketoconazole, or an analgesic agent such as acetylsalicylic acid, acetaminophen, paracetamol, ibuprofen, ketoprofen, indomethacin, diflunisal, naproxen, ketorolac, diclofenac, tolmetin, sulindac, phenacetin, piroxicam, mefamanic acid, dextromethorphan, other non-steroidal anti-inflammatory drugs including salicylates, pharmaceutically acceptable salts thereof or mixtures thereof.

Preferably, a formulation of the invention is prepared by compression. Typically, the core is formed, by compression, and then the coat is prepared by being compressed onto the pre-formed core.

In a preferred aspect, the coat is made up of an admixture of polyvinyl acetate, polyvinylpyrrolidone. The ratio of polyvinyl acetate and polyvinylpyrrolidone in the coat (w/w) is usually between about 6:4 and 9:1, or 7:3 and 9:2, or it is about 8:2.

The coat often includes a binding agent, a preferred binding agent being xanthan gum.

The formulation can be a tablet, and a preferred cross-linked high amylose starch is a chemically-modified, cross-linked high amylose starch prepared by a method comprising:
(a) cross-linking high amylose starch, followed by
(b) chemically modifying the cross-linked high amylose starch, followed by
(c) gelatinization, and
(d) drying to obtain a powder of said controlled release excipient;
wherein said cross-linked high amylose starch is characterized in that upon solubilization in 90% DMSO at 80° C. for about three days and gel permeation chromatography, the height of the peak corresponding to amylose in said cross-linked high amylose starch is at least 90% of that of the peak corresponding to amylose in said high amylose starch prior to (a).

Another process for obtaining a cross-linked high amylose starch for formulations of this invention includes:
(a) cross-linking high amylose starch thereby forming a reaction medium containing a reaction product consisting of a cross-linked high amylose starch slurry;
(b) subjecting said cross-linked high amylose starch slurry from step (a) to chemical modification at a temperature of about 10 to about 90° C. for about 1 to about 72 hours;
(c) neutralizing said reaction medium obtained in step (b) with an acid, washing the slurry formed and optionally dewatering or to form a starch cake or a dry powder;
(d) diluting said slurry or re-slurrifying said starch cake or said dry powder from step
(e) with water to form a slurry at a concentration of about 2% to about 40% w/w, adjusting pH to a desired value between about 3 and about 12, and gelatinizing said slurry at a temperature of about 80 to 180° C. for about 1 second to about 120 minutes; and
(e) drying the thermally treated product obtained in step (d) to obtain said controlled release excipient consisting mainly of chemically modified and cross-linked high amylose starch in form of a powder.

Another process for manufacturing, in an aqueous medium, a controlled release excipient consisting primarily of cross-linked high amylose starch is one including
(a) subjecting high amylose starch to chemical modification at a temperature of about 10 to about 90° C. for about 1 to about 72 hours thereby forming a reaction medium containing a chemically modified high amylose slurry;
(b) cross-linking said chemically modified high amylose starch in said slurry obtained in step (a);
(c) neutralizing said slurry obtained in step (b) with an acid, washing the slurry formed and optionally dewatering to form a starch cake or drying to form dry powder;
(d) diluting said slurry, or re-slurrifying said starch cake or said dry powder from step (c) with water to form a slurry at a concentration of about 2% to about 40% w/w, adjusting pH to a desired value between about 3 and about 12, and gelatinizing said slurry at a temperature of about 80 to 180° C. for about 1 second to about 120 minutes; and
(e) drying the thermally treated product obtained in step (d) to obtain said controlled release excipient consisting mainly of chemically modified and cross-linked high amylose starch in form of a powder.

Another process for obtaining a cross-linked high amylose starch for this invention includes:
(a) cross-linking high amylose starch, followed by
(b) chemically modifying the cross-linked high amylose starch, followed by
(c) gelatinization, and
(d) drying to obtain a powder of said controlled release excipient;
wherein said cross-linked high amylose starch is characterized in that upon solubilization in 90% DMSO at 80° C. for about three days and gel permeation chromatography, the height of the peak corresponding to amylose in said cross-linked high amylose starch is at least 90% of that of the peak corresponding to amylose in said high amylose starch prior to (a).

Another process for obtaining a cross-linked high amylose starch for this invention includes:
(a) cross-linking high amylose starch, followed by
(b) chemically modifying the cross-linked high amylose starch, followed by
(c) gelatinization, and
(d) drying to obtain a powder of said controlled release excipient;
wherein said cross-linked high amylose starch is characterized in that less than about 20% of the amylose present in said high amylose starch prior to (a) is chemically cross-linked to amylopectin.

Another process for obtaining a cross-linked high amylose starch for this invention includes:
(a) cross-linking high amylose starch, followed by
(b) chemically modifying the cross-linked high amylose starch, followed by
(c) gelatinization, and
(d) drying to obtain a powder of said controlled release excipient;
wherein said cross-linked high amylose starch is characterized in that upon solubilization in 90% DMSO at 80° C. for about three days and gel permeation chromatography, less than about 20% of the amylose present prior to (a) is chemically cross-linked to and eluted with amylopectin.

Another process for obtaining a cross-linked high amylose starch for this invention includes:
(a) cross-linking high amylose starch, followed by
(b) chemically modifying the cross-linked high amylose starch, followed by (c) gelatinization, and
(d) drying to obtain a powder of said controlled release excipient;

wherein said cross-linked high amylose starch is characterized in that upon solubilization in 90% DMSO at 80° C. for about three days and gel permeation chromatography, the height of the peak corresponding to amylose is higher than that of the peak corresponding to amylopectin-containing entities.

Another process for obtaining a cross-linked high amylose starch for this invention includes:
(a) cross-linking high amylose starch, followed by
(b) chemically modifying the cross-linked high amylose starch, followed by
(c) gelatinization, and
(d) drying to obtain a powder of said controlled release excipient;

wherein said cross-linked high amylose starch is characterized in that less than about 20% of the amylose present in said high amylose starch prior to (a) is chemically cross-linked to amylopectin.

Another process for obtaining a cross-linked high amylose starch for this invention includes:
(a) cross-linking high amylose starch, followed by
(b) chemically modifying the cross-linked high amylose starch, followed by
(c) gelatinization, and
(d) drying to obtain a powder of said controlled release excipient;

wherein said cross-linked high amylose starch is characterized in that upon solubilization in 90% DMSO at 80° C. for about three days and gel permeation chromatography, less than about 20% of the amylose present prior to (a) is chemically cross-linked to and eluted with amylopectin.

Another process for obtaining a cross-linked high amylose starch for this invention includes:
(a) cross-linking high amylose starch, followed by
(b) chemically modifying the cross-linked high amylose starch, followed by
(c) gelatinization, and
(d) drying to obtain a powder of said controlled release excipient;

wherein said cross-linked high amylose starch is characterized in that upon solubilization in 90% DMSO at 80° C. for about three days and gel permeation chromatography, the height of the peak corresponding to amylose is higher than that of the peak corresponding to amylopectin-containing entities.

Of course, a product having the structure of a cross-linked high amylose starch obtained by one of these processes, even though the manufacturing process is not identical one of these is also within the scope of this invention The core of a formulation of this invention often includes a lubricant which is optionally hydrogenated vegetable oil.

In a preferred aspect, a formulation of the invention is a tablet formulated for oral administration.

In one particular embodiment, the invention is a solid dosage formulation that includes:
a core having a pharmacological agent dispersed in a first controlled-release matrix from which release of the agent is relatively slow; and
a coat formed over the core and comprising said agent dispersed in a second controlled-release matrix, the second controlled-release matrix comprising a physical mixture of polyvinyl acetate and polyvinylpyrrolidone and from which release of the agent is relatively fast.

In another embodiment, the invention provides a solid dosage formulation that includes:
a core comprising a pharmacological agent dispersed in a first controlled-release matrix comprising cross-linked high amylose starch, from which matrix release of the agent is relatively slow; and
a coat formed over the core and comprising a pharmacological agent in a second controlled-release matrix, the second controlled-release matrix comprising a physical mixture of polyvinyl acetate and polyvinylpyrrolidone, and wherein:
release of the agent from the matrix of the core is relatively slow with respect to release of the agent from the matrix of the coat Another aspect of the invention is a solid dosage formulation that includes:
a core comprising a pharmacological agent in a first controlled-release matrix; and
a coat formed over the core and comprising a pharmacological agent in a second controlled-release matrix, the second controlled-release matrix comprising a physical mixture of polyvinyl acetate and polyvinylpyrrolidone, and wherein:
release of the agent from the matrix of the core is relatively slow with respect to release of the agent from the matrix of the coat.

In another aspect, the invention includes a solid dosage formulation comprising a pharmacological agent for release thereof over an extended period of time, the formulation comprising:
a core comprising agent in a first controlled-release release matrix, the controlled-release matrix comprising cross-linked high amylose starch; and
a coat formed over the core and comprising the agent in a second controlled-release matrix, the second controlled-release matrix comprising a physical mixture of polyvinyl acetate and polyvinylpyrrolidone, and wherein:
the agent is present in the core sufficient to obtain release into an aqueous environment, e.g. gastric juices, of no more than 50% of the agent from the formulation within one quarter of the period.

In such a formulation, the period can be between about 12 and about 24 hours, and between about 30% and about 70% of the agent is in the core. The agent in the first matrix and the agent in the second matrix is preferably soluble in water at least to the extent of 1 g/L, or more than 10 g/L, or more than 100 g/L, or more than 500 g/L, or more than 1000 g/L, or more than 2000 g/L. The agent can be an analgesic.

A particular embodiment of the invention includes a solid dosage formulation for use for a period of every four hours, or every six hours, every eight hours, every twelve hours, or every twenty-four hours, the formulation comprising:
a compressed core comprising a pharmacological agent including an amino group, the agent being present as a pharmacologically acceptable salt and being dispersed in a first controlled-release matrix comprising cross-linked high amylose starch; and
a coat formed by compression over the core and comprising the agent in a second controlled-release matrix, the second controlled-release matrix comprising a physical mixture of polyvinyl acetate and polyvinylpyrrolidone, and wherein
release of the agent from the formulation over the period includes a first phase with the average rate of release over the first 5% of the period being between three and eight times the rate of release of the agent half way through the period.

In a particular aspect of this particular embodiment, the ratio of the agent in core to the agent in the coat (w/w) is between 0.2 and about 7, the core is between 20% and 80% by weight agent, the coat is between 15% and 50% by weight agent, and the ratio of the matrix of the coat to the agent of the coat (w/w) is between 0.3 and 7. Further, the preferred agent is tramadol, and preferably the coat includes a binding agent.

In another aspect, the invention is a controlled released tablet comprising:
a compressed core comprising cross-linked high amylose starch having tramadol, or a salt thereof, embedded therein; and
a coat formed over the core by compression, and comprising a physical mixture of polyvinyl acetate, polyvinylpyrrolidone, a binder, tramadol; and wherein:
the ratio of the core/coat (w/w) is between about 0.2 and 0.6;
the ratio of the tramadol in the core to the tramadol in the coat is between about 0.7 and about 1;
the ratio of polyvinyl acetate/polyvinylpyrrolidne (w/w) is between about 6:4 and 9:1; and
the rate of release of tramadol from the coat matrix is at least twice the rate of release of tramadol from the core when measured by a USP Type I apparatus in 50 mM phosphate, pH 6.8, and between 50 and 150 rpm.

The invention includes a method of manufacturing a controlled-release medication, the method comprising:
(i) blending a pharmacological agent and a first matrix material comprising a cross-linked high amylose starch;
(ii) forming the resultant blend of step (i) into a core;
(iii) blending a pharmacological agent and a second matrix material comprising a relatively fast release material with respect to the first matrix material; (iv) forming the resultant blend of step (iii) as a coat onto the exterior of the core.

A method of manufacturing a controlled-release medication of invention can include:
(i) blending a pharmacological agent and a first matrix material;
(ii) forming the resultant blend of step (i) into a core;
(iii) blending a pharmacological agent and a second matrix material, the second matrix material comprising a physical mixture of polyvinyl acetate and polyvinylpyrrolidone and being a relatively fast release material with respect to the first matrix material;
(iv) forming the resultant blend of step (iii) as a coat onto the exterior of the core.

Step (ii) preferably comprises compressing the resultant blend of step (i). Step (iii) can comprise compressing the resultant blend of step (iii) onto the exterior of the core. The agent in the core and the coat is preferably tramadol, the total amount of tramadol in the medication is effective as a daily dosage, and the medication comprises a formulation, as appropriate as defined within this specification.

The invention includes an oral tramadol pharmaceutical composition suitable for once daily administration comprising an effective amount of tramadol or a pharmaceutically acceptable salt thereof providing after a single administration in vivo, a median time to tramadol peak plasma concentration ($T_{max}$) between 2 and 8 hours and a mean peak tramadol plasma concentrations ($C_{max}$) which are less than three times the mean plasma concentration obtained 24 hours after administration ($C_{24h}$) of a single dose of such composition.

Such a composition can be such that said mean peak tramadol plasma concentrations ($C_{max}$) are less than two times the mean plasma concentration obtained 24 hours after administration ($C_{24h}$) of a single dose of such composition.

In another embodiment, the invention is an oral tramadol pharmaceutical composition suitable for successive administration, once daily, comprising an effective amount of tramadol or a pharmaceutically acceptable salt thereof providing in vivo a steady state in which, during a given 24 hour period, a tramadol maximum mean plasma concentration ($C_{max}$) of between 2 and 3 times a tramadol minimum mean plasma concentration ($C_{min}$) is obtained. According to a particular aspect, the mean $C_{max}$ is no greater than 350 ng/ml. The mean plasma concentration of tramadol is preferably less than 90 percent of $C_{max}$ for at least 18 hours of a said 24 hour period.

The invention includes a solid dosage formulation comprising:
a core comprising a pharmacological agent dispersed in a first controlled-release matrix comprising cross-linked high amylose starch; and
a coat formed over the core and comprising said agent dispersed in a second controlled-release matrix, different from the first such that release of the agent from the formulation is biphasic.

According to another aspect, the invention is a solid dosage formulation comprising:
a core comprising a pharmacological agent dispersed in a first controlled-release matrix; and
a coat formed over the core and comprising said agent dispersed in a second controlled-release matrix comprising a physical mixture of polyvinyl acetate and polyvinylpyrrolidone such that release of the agent from the formulation is biphasic.

According to yet another aspect, the invention is a solid dosage formulation comprising:
a core comprising a pharmacological agent dispersed in a controlled-release matrix comprising a cross-linked high amylose starch; and
a coat formed over the core and comprising a pharmacological agent in a second controlled-release matrix comprising a physical mixture of polyvinyl acetate and polyvinylpyrrolidone.

In another embodiment, the invention is a solid dosage formulation comprising:
a core comprising about 50 mg, or about 75 mg or about 100 mg or about 125 mg or about 150 mg or about 175 mg or about 200 mg or about 225 mg or about 250 mg or about 275 mg or about 300 mg or about 325 mg or about 350 mg or about 375 mg or about 400 mg tramadol dispersed in a controlled-release matrix comprising a cross-linked high amylose starch; and
a coat formed over the core and comprising a pharmacological agent in a second controlled-release matrix comprising a physical mixture of polyvinyl acetate and polyvinylpyrrolidone.

The term "comprising" as used herein is used in its open-ended sense, unless the context would dictate otherwise. That is, a formulation comprising first and second matrices and an agent, for example, could thus also include other ingredients, such as a lubricant.

Formulations of the above-described formulations provide advantageous characteristics in vivo, as set out further below. Another aspect of the invention is thus a once daily oral pharmaceutical composition for controlled release of tramadol or a salt thereof, in which the composition, upon initial administration of one dose, provides an onset of analgesic effect within 2 hours, which analgesic effect continues for at least 24 hours after administration.

Another aspect of the invention is a once daily oral pharmaceutical composition for controlled release of tramadol or a salt thereof, wherein the composition, upon initial administration of one dose, provides a mean plasma concentration of at least 100 ng/mL within 2 hours of administration and continues to provide a mean plasma concentration of at least 100 ng/mL for at least 22 hours after administration.

Another aspect of the invention is a once daily oral pharmaceutical composition for controlled release of tramadol or a salt thereof, wherein the composition, upon initial administration of one dose, provides a mean plasma concentration of at least 100 ng/mL within 2 hours of administration and continues to provide a mean plasma concentration of at least 100 ng/mL for at least 23 hours after administration.

In another aspect, the invention is a once daily oral pharmaceutical composition for controlled release of tramadol or a salt thereof, wherein the composition, upon initial administration of one dose, provides a mean plasma concentration of at least 100 ng/mL within 2 hours of administration and continues to provide a mean plasma concentration of at least 100 ng/mL for at least 24 hours after administration.

A once daily oral pharmaceutical composition of the invention, in a preferred aspect, includes about 200 mg of tramadol or a salt thereof.

In yet another aspect, the invention is a once daily oral pharmaceutical composition for controlled release of tramadol or a salt thereof comprising 100 mg of tramadol or a salt thereof, wherein the composition, upon initial administration of one dose, provides a mean plasma concentration of at least 50 ng/mL within 2 hours of administration and continues to provide a mean plasma concentration of at least 50 ng/mL for at least 22 hours after administration.

According to another aspect, the invention provides a once daily oral pharmaceutical composition for controlled release of tramadol or a salt thereof comprising 100 mg of tramadol or a salt thereof, wherein the composition, upon initial administration of one dose, provides a mean plasma concentration of at least 50 ng/mL within 2 hours of administration and continues to provide a mean plasma concentration of at least 50 ng/mL for at least 23 hours after administration.

Another aspect of the invention is a once daily oral pharmaceutical composition for controlled release of tramadol or a salt thereof comprising 300 mg of tramadol or a salt thereof, wherein the composition, upon initial administration of one dose, provides a mean plasma concentration of at least 150 ng/mL within 2 hours of administration and continues to provide a mean plasma concentration of at least 150 ng/mL for at least 22 hours after administration.

Another aspect of the invention is a once daily oral pharmaceutical composition for controlled release of tramadol or a salt thereof comprising 300 mg of tramadol or a salt thereof, wherein the composition, upon initial administration of one dose, provides a mean plasma concentration of at least 150 ng/mL within 2 hours of administration and continues to provide a mean plasma concentration of at least 150 ng/mL for at least 23 hours after administration.

Another aspect of the invention is a once daily oral pharmaceutical composition for controlled release of tramadol or a salt thereof comprising 300 mg of tramadol or a salt thereof, wherein the composition, upon initial administration of one dose, provides a mean plasma concentration of at least 150 ng/mL within 2 hours of administration and continues to provide a mean plasma concentration of at least 150 ng/mL for at least 24 hours after administration.

In another aspect of the A once daily oral pharmaceutical composition for controlled release of tramadol or a salt thereof comprising 200 mg of tramadol or a salt thereof, wherein upon initial administration of 400 mg, the composition provides a mean plasma concentration of at least 200 ng/mL for at least 22 hours after administration.

Another aspect of the invention is a once daily oral pharmaceutical composition for controlled release of tramadol or a salt thereof comprising 200 mg of tramadol or a salt thereof, wherein upon initial administration of 400 mg, the composition provides a mean plasma concentration of at least 190 ng/mL for at least 23 hours after administration.

Another aspect of the invention is a once daily oral pharmaceutical composition for controlled release of tramadol or a salt thereof comprising 200 mg of tramadol or a salt thereof, wherein upon initial administration of 400 mg, the composition provides a mean plasma concentration of at least 180 ng/mL for at least 24 hours after administration.

The invention also provides a once daily oral pharmaceutical composition wherein the mean maximum plasma concentration ($C_{max}$) is less than 100 ng/mL.

Further, a once daily oral pharmaceutical composition of the invention can provide a mean maximum plasma concentration ($C_{max}$) is less than 300 ng/mL, or a mean maximum plasma concentration ($C_{max}$) is less than 200 ng/mL.

A once daily oral pharmaceutical composition of the invention can be such that the mean maximum plasma concentration ($C_{max}$) is less than 2.2 times the mean plasma concentration obtained 24 hours after administration ($C_{24h}$).

The once daily oral pharmaceutical composition can be such that the mean maximum plasma concentration ($C_{max}$) is less than 300 ng/mL.

The mean maximum plasma concentration ($C_{max}$) can be less than two times the mean plasma concentration obtained 24 hours after administration ($C_{24h}$).

The mean maximum plasma concentration ($C_{max}$) can be less than 2.3 times the mean plasma concentration obtained 24 hours after administration ($C_{24h}$).

The once daily oral pharmaceutical composition of the invention can provide a median time to the mean maximum plasma concentration ($t_{max}$) of between 2 and 10 hours, or between 3 and 6 hours, or between 5 and 6 hours.

The invention also provides a once daily oral pharmaceutical composition for controlled release of tramadol or a salt thereof comprising 200 mg of tramadol or a salt thereof, wherein the composition, upon initial administration of one dose, provides an O-desmethyltramadol mean plasma concentration of at least 24 ng/mL within 2 hours of administration and continues to provide an O-desmethyltramadol mean plasma concentration of at least 25 ng/mL for at least 24 hours after administration.

According to another embodiment, the invention provides a once daily oral pharmaceutical composition for controlled release of tramadol or a salt thereof comprising 100 mg of tramadol or a salt thereof, wherein the composition, upon initial administration of one dose, provides an O-desmethyltramadol mean plasma concentration of at least 11 ng/mL within 2 hours of administration and continues to provide an O-desmethyltramadol mean plasma concentration of at least 12 ng/mL for at least 24 hours after administration.

According to another embodiment, the invention provides a once daily oral pharmaceutical composition for controlled release of tramadol or a salt thereof comprising 300 mg of tramadol or a salt thereof, wherein the composition, upon initial administration of one dose, provides an O-desmethyltramadol mean plasma concentration of at least 32 ng/mL within 2 hours of administration and continues to provide an O-desmethyltramadol mean plasma concentration of at least 32 ng/mL for at least 24 hours after administration.

In another embodiment, the invention is a once daily oral pharmaceutical composition for controlled release of tramadol or a salt thereof comprising 200 mg of tramadol or a salt thereof, wherein upon initial administration of 400 mg, the composition provides an O-desmethyltramadol mean plasma concentration of at least 50 ng/mL within 2 hours of administration and continues to provide an O-desmethyltramadol mean plasma concentration of at least 50 ng/mL for at least 24 hours after administration.

One object of the present invention is to provide flexible dosing options for patients with different analgesic requirements with a once daily formulation.

One embodiment of the present invention is to provide a once daily formulation which upon initial ingestion of a dose of 100 mg would provide the desired early onset of action but achieve mean tramadol plasma concentrations of at least 45 ng/mL between 2 and 24 hours.

A further embodiment of the present invention is to provide a once daily formulation which upon initial ingestion of a dose of 200 mg would provide the desired early onset of action but achieve mean tramadol plasma concentrations of at least 100 ng/mL between 2 and 24 hours.

A further embodiment of the present invention is to provide a once daily formulation which upon initial ingestion of a dose of 300 mg would provide the desired early onset of action but achieve mean tramadol plasma concentrations of at least 150 ng/mL between 2 and 24 hours.

A further embodiment of the present invention is to provide a once daily formulation which upon initial ingestion of a dose of 400 mg would provide the desired early onset of action but achieve mean tramadol plasma concentrations of at least 180 ng/mL between 2 and 24 hours.

A further embodiment of the present invention is to provide a once daily formulation which upon initial ingestion of a dose would provide a $C'_{max}$ to dose ratio of from about 0.90 to about 1.0.

A further embodiment of the present invention is to provide a once daily formulation which upon initial ingestion of a dose would provide a tramadol plasma concentration which rises steadily until peak tramadol concentrations are attained at a $T_{max}$ of about 4 hours to about 6 hours. Preferably, the $T_{max}$ occurs at about 5 hours to about 5.5 hours.

A further embodiment of the present invention is to provide a once daily formulation which upon initial ingestion of a dose would provide a tramadol plasma concentration which, after $T_{max}$, declines in a slow but steady manner, reflecting continuing absorption in addition to elimination processes. Preferably, the decline in the tramadol plasma concentration after $T_{max}$ occurs in a log-linear fashion with a mean apparent terminal elimination half-life of between about 5.5 hours and about 6.5 hours.

A further embodiment of the present invention is to provide a once daily formulation which upon initial ingestion of a dose would provide a tramadol plasma concentration which, after $T_{max}$, declines in a slow but steady manner, reflecting continuing absorption in addition to elimination processes, and which absorption continues for at least 20 hours after $T_{max}$.

A further embodiment of the present invention is to provide a once daily formulation which upon initial ingestion of a dose provides a tramadol plasma concentration which, after $T_{max}$, declines in a log-linear fashion with an apparent terminal elimination rate constant ($\lambda_z$) of about 0.12 h$^{-1}$ for the tramadol plasma concentration.

A further embodiment of the present invention is to provide a once daily formulation which upon initial ingestion of a dose would provide a mean residence time (MRT) of tramadol ranging from about 15 hours and about 18 hours.

A further embodiment of the present invention is to provide a once daily formulation which upon initial ingestion of a dose would provide a half value duration (HVD) of tramadol which ranges from about 22.5 hours to about 25.4 hours.

A further embodiment of the present invention is to provide a once daily formulation which upon initial ingestion of a dose would provide a $C'_{max}$ to $AUC_{0-\infty}$ ratio of from about 0.04 h$^{-1}$ to about 0.06 h$^{-1}$. Preferably, the $C'_{max}$ to $AUC_{0-\infty}$ ratio is from about 0.04 h$^{-1}$ to about 0.05 h$^{-1}$. The ratio $C'_{max}/AUC_{0-\infty}$ is used for evaluating the rate of drug absorption.

A further embodiment of the present invention is to provide a once daily formulation which upon initial ingestion of a dose would provide a mean $AUC_{0-24}$ with respect to the tramadol plasma concentration which increases proportionally with dose over the range of dosage strengths of 100 mg to 300 mg of the controlled release composition.

A further embodiment of the present invention is to provide a once daily formulation which upon initial ingestion of a dose of 100 mg would provide a mean $AUC_{0-Tmax}$ of from about 610 ng·h/mL to about 630 ng·h/mL.

A further embodiment of the present invention is to provide a once daily formulation which upon initial ingestion of a dose of 200 mg would provide a mean $AUC_{0-Tmax}$ of from about 910 ng·h/mL to about 920 ng·h/mL.

A further embodiment of the present invention is to provide a once daily formulation which upon initial ingestion of a dose of 300 mg would provide a mean $AUC_{0-Tmax}$ of from about 1570 ng·h/mL to about 1590 ng·h/mL.

A further embodiment of the present invention is to provide a once daily formulation which upon initial ingestion of a dose provides a mean ratio of $AUC_{0-24}/AUC_{0-\infty}$ of tramadol plasma concentration which ranges between about 70% and about 85%. Preferably, the mean ratio of $AUC_{0-24}/AUC_{0-\infty}$ of tramadol plasma concentration ranges between about 74% and about 80%. As a result, about 15% to about 30% of the administered dose is still circulating in the plasma 24 hours post-dose, depending on the dose administered.

A further embodiment of the present invention is to provide a once daily formulation which upon initial ingestion of a dose would provide a ratio of the $C'_{max}$ to the dose released to the blood plasma in the first 24 hours (that is, $AUC_{0-24}/AUC_{0-\infty}$ multiplied by the dose) of from about 1.10 to about 1.35. Preferably the ratio is from about 1.15 to about 1.31.

A further embodiment of the present invention is to provide a once daily formulation which upon initial ingestion of a dose, would provide a ratio of the $C'_{max}/T_{max}$ to the dose administered of from about 0.10 to about 0.20. Preferably the ratio is from about 0.12 to about 0.19.

A further embodiment of the present invention is to provide a once daily formulation which upon initial ingestion of a dose would provide a slope in ng/ml-hr following the peak blood plasma concentration level, which does not exceed a factor of about 0.035 of the total dose administered in mg. Preferably, the factor is about 0.03.

A further embodiment of the present invention is to provide a once daily formulation which upon initial ingestion of a dose would provide a ratio of the $C'_{max}$ calculated with respect to the blood plasma concentration of O-desmethyltramadol, to the dose of tramadol from about 0.19 to about 0.22. Preferably the ratio is from about 0.20 to 0.21.

A further embodiment of the present invention is to provide a once daily formulation which upon initial ingestion of a dose would provide an O-desmethyltramadol plasma concentration which rises steadily until peak tramadol concentrations are attained at a $T_{max}$ of about 8 hours to about 16 hours.

A further embodiment of the present invention is to provide a once daily formulation which upon initial ingestion of a dose would provide an O-desmethyltramadol plasma concentration which, after $T_{max}$, declines in a slow but steady manner, reflecting continuing tramadol absorption and subsequent metabolite formation in addition to elimination processes. Preferably, the decline in the O-desmethyltramadol plasma concentration occurs in a log-linear fashion with a mean apparent terminal elimination half-life of between about 6.7 hours and about 8.1 hours.

A further embodiment of the present invention is to provide a once daily formulation which upon initial ingestion of a dose would provide, after $T_{max}$, the formation of metabolite for at least 18 hours.

A further embodiment of the present invention is to provide a once daily formulation which upon initial ingestion of a dose would, after $T_{max}$, provide a decline in the O-desmethyltramadol plasma concentration in a log-linear fashion with an apparent terminal elimination rate constant ($\lambda_z$) for O-desmethyltramadol concentration of about 0.1 $h^{-1}$.

A further object of the invention is to provide a once daily formulation which upon initial ingestion of 100 mg, 200 mg and 300 mg strengths provides a half value duration (HVD) of O-desmethyltramadol plasma concentration which ranges from 25.6 to 28.1 hours.

A further embodiment of the present invention is to provide a once daily formulation which upon initial ingestion of a dose would provide a half value duration (HVD) of O-desmethyltramadol which ranges from about 25.6 hours to about 28.1 hours.

A further embodiment of the present invention is to provide a once daily formulation which upon initial ingestion of a dose would provide a $C'_{max}$ to $AUC_{0-\infty}$ ratio calculated with respect to the O-desmethyltramadol plasma concentration, of about 0.04 $h^{-1}$. The ratio $C'_{max}/AUC_{0-\infty}$ is used for evaluating the rate of metabolite formation.

A further embodiment of the present invention is to provide a once daily formulation which upon initial ingestion of a dose would provide a mean $AUC_{0-24}$ calculated with respect to the O-desmethyltramadol plasma concentration, which increases proportionally with dose over the range of dosage strengths of 100 mg to 300 Mg of the controlled release composition.

A further embodiment of the present invention is to provide a once daily formulation which upon initial ingestion of a dose of 100 mg would provide a mean $AUC_{0-Tmax}$ with respect to the O-desmethyltramadol plasma concentration of from about 175 ng·h/mL to about 180 ng·h/mL.

A further embodiment of the present invention is to provide a once daily formulation which upon initial ingestion of a dose of 200 mg would provide a mean $AUC_{0-Tmax}$ with respect to the O-desmethyltramadol plasma concentration of from about 530 ng·h/mL to about 550 ng·h/mL.

A further embodiment of the present invention is to provide a once daily formulation which upon initial ingestion of a dose of 300 mg would provide a mean $AUC_{0-Tmax}$ with respect to the O-desmethyltramadol plasma concentration of from about 580 ng·h/mL to about 590 ng·h/mL.

A further embodiment of the present invention is to provide a once daily formulation which upon initial ingestion of a dose provides a mean ratio of $AUC_{0-24}/AUC_{0-\infty}$ of O-desmethyltramadol plasma concentration which ranges between about 65% and about 80%. Preferably, the mean ratio of $AUC_{0-24}/AUC_{0-\infty}$ of O-desmethyltramadol plasma concentration ranges between about 68% and about 75%. As a result, about 25% to about 32% of the active metabolite is still circulating in the plasma 24 hours post-dose.

A further embodiment of the present invention is to provide a once daily formulation which upon initial ingestion of a dose would provide a ratio of the $C'_{max}$ calculated with respect to the O-desmethyltramadol plasma concentration, to the O-desmethyltramadol blood plasma concentration in the first 24 hours ($AUC_{0-24}/AUC_{0-\infty}$ multiplied by the dose of tramadol) of from about 0.0025 to about 0.0035. Preferably the ratio is from about 0.0027 to about 0.0031.

The present invention may be understood more fully by reference to the following detailed description and illustrative examples which are intended to exemplify non-limiting embodiments of the invention.

DESCRIPTION OF THE DRAWINGS

Various features and advantages of the present invention will become clear from the more detailed description given below with reference to the accompanying drawings, in which.

DETAILED DESCRIPTION OF THE INVENTION

Core

Figure 1:
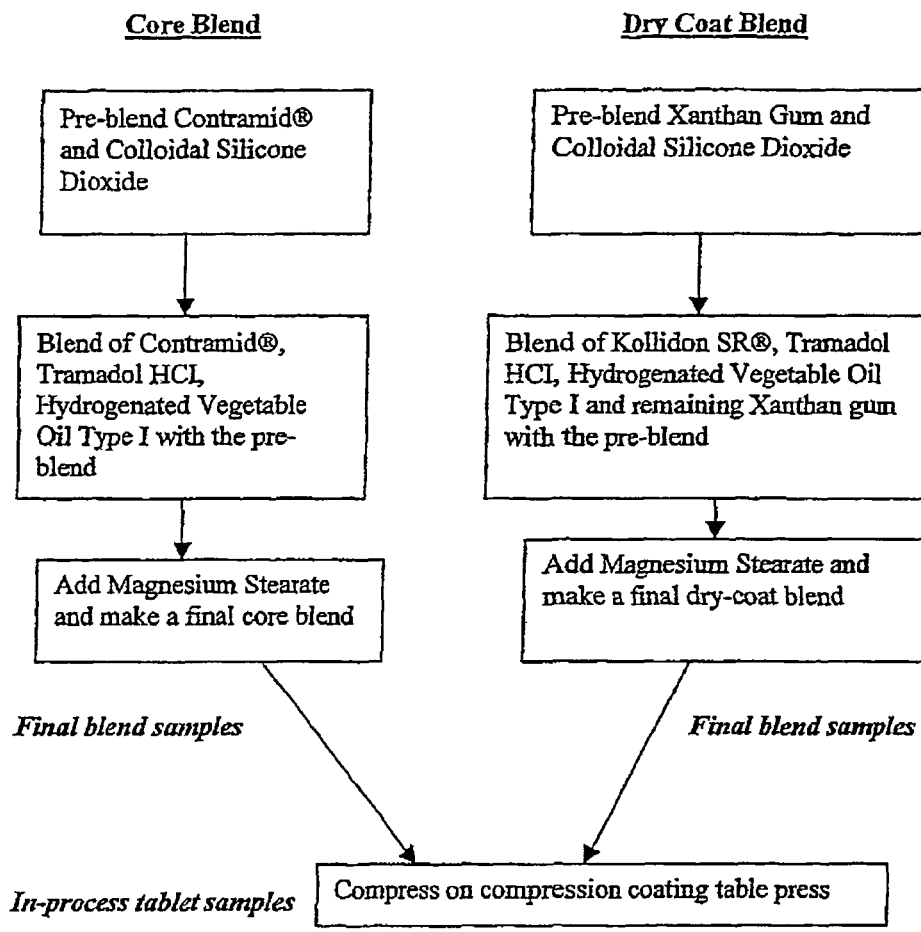
FIG. 1: Flow diagram showing manufacturing process for tablets.

The core of a tablet of the invention includes at least one active ingredient and a matrix, these components associated in such a way that release of the pharmaceutical ingredient from the matrix is controlled. In a specific embodiment, the matrix of the core is a cross-linked high amylose starch known under the name Contramid®, and described most recently in U.S. Pat. No. 6,607,748 (Lenaerts et al.), which issued Aug. 19, 2003. A preferred formulation in the context of this invention is provided in the specification of U.S. Pat. No. 6,607,748.

Preferably, the core is formed by admixing the ingredients (in granular or powder form) and then compressing the mixture to form the core over which the coat is subsequently formed. The weight of the core can be any percentage of the weight of the total composition between 10% and 80%. The preferred percentage depends, upon other things, the total dosage of the pharmaceutical agent. In a particular embodiment described further below, a tablet contains 100 mg tramadol hydrochloride and the core is about 26% of the total weight of the tablet. In another embodiment, a tablet contains 200 mg tramadol hydrochloride and the core makes up about 33% of the total weight of the tablet. In yet another embodiment, a tablet contains 300 mg tramadol hydrochloride, and the core contributes 33% to the total weight of the tablet.

Active Agent in the Core

An active pharmaceutical ingredient is present in the core of the composition of the present invention. A suitable pharmaceutical ingredient of the present invention is any such ingredient that is desired to be delivered in a sustained-release dosage form. A comprehensive list of suitable pharmaceutical agents can be found in *The Merck Index*, 12$^{th}$ Ed. Preferably, the pharmaceutical ingredient is, but not limited to, isonicotinic acid hydrazide, sodium salicylate, pseudoephedrine hydrochloride, pseudoephedrine sulfate, acetaminophen or diclofenac sodium, verapamil, glipizide, nifedipine, felodipine, betahistine, albuterol, acrivastine, omeprazole, misoprostol, Tramadol®, oxybutynin, trimebutine, ciprofloxacin, and salts thereof. In addition, the pharmaceutical agent can be an antifungal agent, such as ketoconazole, or an analgesic agent such as acetylsalicylic acid, acetaminophen, paracetamol, ibuprofen, ketoprofen, indomethacin, diflunisal, naproxen, ketorolac, diclofenac, tolmetin, sulindac, phenacetin, piroxicam, mefamanic acid, dextromethorphan, other non-steroidal anti-inflammatory drugs including salicylates, pharmaceutically acceptable salts thereof or mixtures thereof. Pro-drugs are part of the invention.

The solubility of the pharmaceutical agent in aqueous solution can be a wide variety of values. The aqueous solubility of the pharmaceutical agent can be less than $10^{-3}$ g/L, more than $10^{-3}$ g/L, more than $10^{-2}$ g/L, more than $10^{-1}$ g/L, more than 1 g/L, more than 10 g/L, more than 100 g/L, more than 500 g/L, more than 1000 g/L, or more than 2000 g/L. Preferably, the solubility is more than 100 g/L. More preferably, the solubility is more than 500 g/L. Most preferably, the solubility is more than 1000 g/L.

The pharmaceutical agent can meet a variety of dosage requirement For example, the dosage requirement of the pharmaceutical agent can be less than 1 mg/dosage unit, more than 1 mg/dosage unit, more than 10 mg/dosage unit, more than 100 mg/dosage unit, more than 200 mg/dosage unit, more than 300 mg/dosage unit, more than 400 mg/dosage unit, more than 500 mg/dosage unit, or more than 1000 mg/dosage unit. Preferably, the pharmaceutical agent is more than 50 mg/dosage unit. More preferably, the pharmaceutical agent is 100 mg/dosage unit, or more, e.g. 150 mg/dosage unit, or 200 mg/dosage unit, or 250 mg/dosage unit, or 300 mg/dosage unit, or more.

Particular embodiments include a core containing tramadol hydrochloride in which the core contains between about 10% and 90% of the total tramadol present in the tablet, e.g. about 45 mg of a 100 mg strength tablet (45% of the tablet total), or about 90 of a 200 mg strength tablet (45% of the tablet total), or about 151 mg of a 300 mg strength tablet (50% of the tablet total).

Matrix of the Core

The release from the formulation of an active pharmaceutical ingredient located in the core is slower than the release of an active pharmaceutical ingredient located in the matrix of the coat. A preferred matrix of the core is cross-linked high amylose starch, known under the name Contramid® and described in U.S. Pat. No. 6,607,748. In particular embodiments, the matrix makes up between about 10% and about 90% by weight of the core i.e., the ratio of the matrix of the core to the active ingredient of the core (w/w) is between about 0.1 and about 10, or between about 0.2 and about 9, or between about 0.2 and about 8, or between about 0.3 and about 7, or between about 0.4 and about 6, or between about 0.5 and about 5, or between about 0.6 and about 4, or between about 0.7 and about 4 or between about 1 and about 4, or between about 1 and about 3 and about 1.5 and about 2.5. In one particular embodiment, the core totals about 90 mg, of which about 44 mg is Contramid®, and 45 mg is tramadol hydrochloride. In this case, Contramid® thus makes up about 49 weight percent of the core.]

Optional Components

The core composition of the present invention may optionally include a pharmaceutically acceptable carrier or vehicle. Such carriers or vehicles are known to those skilled in the art and are found, for example, in *Remingtons's Pharmaceutical Sciences*, 14$^{th}$ Ed. (1970). Examples of such carriers or vehicles include lactose, starch, dicalcium phosphate, calcium sulfate, kaolin, mannitol and powdered sugar. Additionally, when required, suitable binders, lubricants, and disintegrating agents can be included. If desired, dyes, as well as sweetening or flavoring agents can be included.

The core composition of the present invention may optionally include accessory ingredients including, but not limited to dispersing agents such as microcrystalline cellulose, starch, cross-linked starch, cross-linked poly(vinyl pyrrolidone), and sodium carboxymethyl cellulose; flavoring agents; coloring agents; binders; preservatives; surfactants and the like.

The core can, optionally, also include one or more suitable binders known to one of ordinary skilled in the art Suitable forms of microcrystalline cellulose, for example, MCCPH101, MCC-102, MCC-105, etc.

Suitable lubricants, such as those known to the skilled person, may also be included. For example, magnesium stearate, vegetable oil, talc, sodium-stearyl fumarate, calcium stearate, stearic acid, etc.

Suitable glidants, known in the art, may also be included. Examples of such glidants include, but are not limited to talc, colloidal silicon dioxide, etc.

Proportion

The active agent is present at levels ranging from about 1 to about 90 wt. % of the total weight of the core, preferably from about 10 to about 70 wt. % of the total composition of the core, more preferably from about 20 to about 60 wt. % of the total composition of the core, and probably most often between about 30 to about 50 wt. % of the total composition of the core.

Of course, the total amount of all components is 100 wt. %, and those of ordinary skill in the art can vary the amounts within the stated ranges to achieve useful compositions.

Coat

The coat of the dosage form includes a physical mixture of polyvinyl acetate and polyvinylpyrrolidone and the active pharmaceutical ingredient(s) of the coat. The coat can also include a cross-linked high amylose starch, e.g. Contramid®, and other optional components. In a preferred embodiment, the coat is formed by dry compression. The weight of the coat can be any percentage of the weight of the total composition between about 10% and about 90%, but is preferably in the higher part of this range. The coat thus usually makes up between about 20% to about 90%, (w/w) of a tablet of the invention, or about 25% to about 90%, or about 30% to about 85%, or about 35% to about 85%, or about 40% to about 85%, or about 45% to about 85%, or about 45% to about 90%, or about 50% to about 90% or about 50% to about 85%, or about 55% to about 90%, or about 55% to about 85%, or about 55% to about 80%, or about 60% to about 90%, or about 60% to about 85%, or about 60% to about 80%, or about 60% to about 75%, or about 65% to about 90%, or about 65% to about 85%, or about 65% to about 80%, or about 65% to about 75%, or about 65% or about 70% or about 75%. The coat often includes an optional binding agent.

Polyvinyl Acetate and Polyvinylpyrrolidone of the Coat

The weight percentage of the polyvinyl acetate/polyvinylpyrrolidone mixture in the coat can be anywhere within a wide range of values. Depending on the solubility in water of the active ingredient in the coat, the amount of the polyvinyl acetate/polyvinylpyrrolidone mixture in the coat can be adjusted. United States Patent Publication No. 2001/0038852 describes ways in which such adjustments can be made. For example, for active ingredients that are soluble to extremely soluble in water, polyvinyl acetate/polyvinylpyrrolidone mixture can be about 20 to about 80 wt. % of the coat, preferably about 30 to about 65 wt. %, or about 40 to about 55 wt. %. In a particular embodiment described below, Kollidon™ SR makes up about 45% by weight of a coat that is about 31% by weight tramadol hydrochloride and about 23% xanthan gum. For active ingredients that are sparingly soluble to slightly soluble in water, the amount of polyvinyl acetate/polyvinylpyrrolidone mixture is often lower, as described in United States Patent Publication No. 2001/0038852.

The weight ratio of polyvinyl acetate to polyvinylpyrrolidone in the polyvinyl acetate/polyvinylpyrrolidone mixture can be a wide range of values. Preferably, such ratio is between about 6:4 and 9:1; more likely between about 7:3 and 6:1, even more preferably about 8:2.

The molecular weight of the polyvinyl acetate component in the polyvinyl acetate/polyvinylpyrrolidone mixture can be a wide range of values Preferably, the average molecular weight of the polyvinyl acetate is about 100 to about 10,000,000; or about 1,000 to about 1,000,000; or about 10,000 to about 1,000,000; or about 100,000 to about 1,000,000; or about 450,000.

The molecular weight of the polyvinylpyrrolidone component in the polyvinyl acetate/polyvinylpyrrolidone mixture can be a wide range of values The average molecular weight of the polyvinylpyrrolidone can be from about 100 to about 10,000,000; or about 1,000 to about 1,000,000; or about 5,000 to about 500,000; or about 10,000 to about 100,000; or about 50,000.

The polyvinyl acetate and polyvinylpyrrolidone mixture can be prepared by a variety of processes including simply mixing powders of polyvinylpyrrolidone and polyvinyl acetate. In a preferred embodiment, such mixture is spray dried powder of a colloidal dispersion of polyvinyl acetate and polyvinylpyrrolidone solution. Optionally, sodium lauryl sulfate is used as a stabilizer in order to prevent agglomeration during spray drying process and/or colloidal silica is used to improve the flow properties of the polyvinyl acetate/polyvinylpyrrolidone mixture. Optionally, polyvinyl acetate and polyvinylpyrrolidone can be formed in a random or a block copolymer.

Optional Components

Suitable binding agents for the present invention include, but are not limited to, plant extracts, gums, synthetic or natural polysaccharides, polypeptides, alginates, synthetic polymers, or a mixture thereof.

Suitable plant extracts to be used as gelling agents include, but are not limited to, agar, ispaghula, psyllium, cydonia, ceratonia or a mixture thereof.

Suitable gums to be used as gelling agents include, but are not limited to, xanthan gum, guar gum, acacia gum, ghatti gum, karaya gum, tragacanth gum or a mixture thereof.

Suitable synthetics or natural hydrophilic polysaccharides to be used as gelling agents include, but are not limited to, hydroxyalkylcelluloses, cellulose ethers, cellulose esters, nitrocelluloses, dextrin, agar, carrageenan, pectin, furcellaran, starch or starch derivatives, cross-linked high amylose starch, or a mixture thereof.

Suitable polypeptides to be used as gelling agents include, but are not limited to, gelatin, collagen, polygeline or a mixture thereof.

Suitable alginates to be used as gelling agents include, but are not limited to, alginic acid, propylene glycol alginate, sodium alginate or a mixture thereof.

Suitable synthetic polymers to be used as gelling agents include, but are not limited to, carboxyvinyl polymer, polyvinyl alcohol, polyvinyl pyrrolidone, polyethelene oxide, polyethylene glycols, copolymers of ethylene oxide and propylene oxide and their copolymers or a mixture thereof.

In a preferred embodiment, the gelling agent is a gum such as xanthan gum, guar gum, acacia gum, ghatti gum, karaya gum, tragacanth gum or a mixture thereof, PEO 7,000,000 and HPMC K100 M.

In a most preferred embodiment, the gelling agent is xanthan gum.

Active Agent of the Coat

A suitable active pharmaceutical ingredient of the present invention is any active agent that it is desired to be delivered in a sustained-release dosage form. A comprehensive list of suitable pharmaceutical agents can be found in *The Merck Index*, 12$^{th}$ Ed. Preferably, the pharmaceutical agent is, but not limited to, isonicotinic acid hydrazide, sodium salicylate, pseudoephedrine hydrochloride, pseudoephedrine sulfate, acetaminophen or diclofenac sodium, verapamil, glipizide, nifedipine, felodipine, betahistine, albuterol, acrivastine, omeprazole, misoprostol, Tramadol®, oxybutynin, trimebutine, ciprofloxacin, and salts thereof. In addition, the pharmaceutical agent can be an antifungal agent, such as ketoconazole, or an analgesic agent such as acetylsalicylic acid, acetaminophen, paracetamol, ibuprofen, ketoprofen, indomethacin, diflunisal, naproxen, ketorolac, diclofenac, tolmetin, sulindac, phenacetin, piroxicam, mefamanic acid, dextromethorphan, other non-steroidal anti-inflammatory drugs including salicylates, pharmaceutically acceptable salts thereof or mixtures thereof.

The solubility of the pharmaceutical agent in aqueous solution can be a wide variety of values. The aqueous solubility of the pharmaceutical agent can be less than $10^{-3}$ g/L, more than $10^{-3}$ g/L, more than $10^{-2}$ g/L, more than $10^{-1}$ g/L, more than 1 g/L, more than 10 g/L, more than 100 g/L, more than 500 g/L, more than 1000 g/L, or more than 2000 g/L. Preferably, the solubility is more than 100 g/L. More preferably, the solubility is more than 500 g/L. or even 1000 g/L.

The pharmaceutical agent can meet a variety of dosage requirements. For example, the dosage requirement of the pharmaceutical agent can be less than 1 mg/dosage unit, more than 1 mg/dosage unit, more than 10 mg/dosage unit, more than 100 mg/dosage unit, more than 200 mg/dosage unit, more than 300 mg/dosage unit, more than 400 mg/dosage unit, more than 500 mg/dosage unit, or more than 1000 mg/dosage unit. Preferably, the pharmaceutical agent is more than 50 mg/dosage unit. More preferably, the pharmaceutical agent is more than 100 mg/dosage unit. Most preferably, the pharmaceutical agent is more than 200 mg/dosage unit.

The coat can be between about 5% and about 90% by weight active pharmaceutical ingredient, or between about 5% and about 80% by weight api, or between about 10% and about 70% by weight api, or between about 10% and about 60% by weight api, or between about 15% and about 50% by weight api, or between about 15% and about 45% by weight api, or between about 15% and about 40% by weight api, or between about 20% and about 35% by weight api, or between about 20% and about 30% by weight api.

In particular embodiments, described further below, the weight of tramadol from a 100 mg tramadol tablet is about 21% by weight of the coat. The weight of tramadol from a 200 mg tablet is about 31% by weight of the coat. The weight of tramadol from a 300 mg tablet is about 30% by weight of the coat.

Routes of Administration

The tablet composition of the present invention can be administered through, but not limited to, a number of routes such as oral, sublingual, and rectal. The preferred route of administration of the compositions of the present invention is oral.

Compositions of the present invention that are suitable for oral administration may be presented as discrete units such as tablets or granules. Preferably, the compositions of the present invention are presented in a tablet form Such tablets may be conventionally formed by compression or molding. Compressed tablets may be prepared by compressing in a suitable machine the mixture of one or more components described above. Molded tablets may be made by molding in a suitable machine the above components, which can be optionally moistened with an inert liquid diluent. The tablets may optionally be coated and/or have other identifying indicia visible to the consumer. A tablet can also be in a variety of forms, e.g, uncoated, dry coated, or film coated, etc. A tablet can also be in a variety of shapes (e.g, oval, sphere, etc.) and sizes. A comprehensive discussion of tablets can be found in references such as *The Theory and Practice of Industrial Pharmacy* by Lachman et al., $3^{rd}$ Ed. (Lea & Febiger, 1986).

Dissolution Profile of Sustained-Release Composition

The active agent of the composition exhibits the following in vitro dissolution profile when measured with a USP Type I apparatus in 50 mM phosphate, pH 6.8, and stirring between 50 and 150 rpm:

an average rate of between 10% and 30% per hour of the agent is released between 0 and 2 hours when tested in vitro using a USP Type I apparatus in 50 mM phosphate, pH 6.8, and stirring between 50 and 150 rpm; or between 10% and 40% of the agent is released from the formulation between 0 and about 2 hours of measurement, between about 30% and 60% of the agent is released from the formulation between 2 and about 7 hours of the measurement, between about 50% and 80% of the agent is released from the formulation between 7 and about 12 hours of measurement, and between about 80% and 100% of the agent is released from the formulation after about 20 hours of measurement; or more preferably between 15% and 35% of the agent is released from the formulation between at 2 hours of measurement, between about 40% and 60% of the agent is released from the formulation between at 7 hours of the measurement, between about 60% and 80% of the agent is released from the formulation at 12 hours of measurement, and between about 85% and 100% of the agent is released from the formulation after about 20 hours of measurement, or between 20% and 40% of the agent is released from the formulation between at 2 hours of measurement, between about 40% and 60% of the agent is released from the formulation between at 7 hours of the measurement, between about 60% and 80% of the agent is released from the formulation at 12 hours of measurement, and between about 85% and 100% of the agent is released from the formulation after about 20 hours of measurement.

The present invention will be more readily understood by referring to the following examples which are given to illustrate the invention rather than to limit its scope.

EXAMPLES

The cross-linked high amylose starch used in the these examples is made by a process comprising the steps of crosslinking and chemically modifying, followed by gelatinization and drying. Such process is described in more detail in U.S. Pat. No. 6,607,748 (Lenaerts et al.), which issued Aug. 19, 2003, and known in the marketplace under the name Contramid®. and described in Examples I and II.

Example I

A. Cross-Linking

High amylose starch (30.0 kg) containing about 70% w/w of amylose (Cl AmyloGel 03003) is placed in a reactor. To this reactor is added water (55.0 1) containing sodium hydroxide (30.0 g) and sodium sulfate (2.40 kg). The resulting slurry is heated to a temperature of 30° C. Phosphorus oxychloride (22.5 g) is added to the reaction mixture which is reacted for one hour.

B. Chemical Modification, Hydroxyproylation

The crude reaction mixture from Part A is transferred into a hydroxypropylation reactor. The reaction mixture is heated to 40° C. over 30 minutes and the reaction is purged with nitrogen. After a full purge, propylene oxide (1.80 kg) is added. The reaction mixture is kept at 40° C. for 20 hours. The reaction mixture is neutralized with 0.1N $H_2SO_4$ (1:2 v/v) to a pH of 5.5. The starch slurry is washed with a basket-centrifuge at a speed of 1200 rpm. The obtained starch cake is re-slurrfied in 35 l of water and centrifuged a second time. The resulting starch cake is dried in a flash dryer at an inlet temperature of 160° C. and an outlet temperature of 60° C.

C. Gelatinization

The modified granular starch cake is diluted in demineralized water in order to form a slurry at a concentration of about 8% calculated on dry substance. The resulting slurry has a relative density of 1.032 kg/l compared to water. The pH of the modified starch slurry is adjusted to 6.0. The slurry is then heated to 160° C. by direct steam injection (Schlick Model 825). The temperature variation is not higher than ±1° C. The slurry is held in a holding column for a period of 4 minutes at a temperature of 160° C. and a pressure of about 5.5 bar. The pressure is then reduced to atmospheric by passing through a flash. The slurry is then contained at 95° C. in a hold tank D. Spray-Drying The drying of the slurry from Part C is carried out using a Niro FSD 4 spray-drying tower equipped with a 0.8 mm nozzle and fed at 10 l/hour. The inlet temperature is fixed at 300° C. and the outlet temperature of 120° C. The obtained powder is a controlled release excipient with the following properties:

| Properties | |
|---|---|
| Moisture Content | 4.5% |
| Bulk Density | 150 g/l |
| Packed Density | 210 g/l |
| pH | 5.4 |
| Particle Size Peak Value (Laser Particle Sizer-Sympatec) | 50 μm |

Example II

A. Cross-Linking

High amylose starch (30.0 kg) containing about 70% w/w of amylose (Cl AmyloGel 03003) is placed in a reactor. To this reactor is added water (55.0 l) containing sodium hydroxide (30.0 g) and sodium sulfate (2.40 kg). The resulting slurry is heated to a temperature of 30° C. Sodium trimetaphosphate (45 g) is added to the reaction mixture which is reacted for one hour.

B. Chemical Modification, Hydroxyproylation

The crude reaction mixture from Part A is transferred into a hydroxypropylation reactor. The reaction mixture is heated to 40° C. over 30 minutes and the reaction is purged with nitrogen. After a full purge, propylene oxide (1.80 kg) is added. The reaction mixture is kept at 40° C. for 20 hours. The reaction mixture is neutralized with 0.1N $H_2SO_4$ (1:2 v/v) to a pH of 5.5. The starch slurry is washed with a basket-centrifuge at a speed of 1200 rpm. The obtained starch cake is re-slurrified in 35 l of water and centrifuged a second time. The resulting starch cake is dried in a flash dryer at an inlet temperature of 160° C. and an outlet temperature of 60° C.

C. Gelatinization

The modified granular starch cake is diluted in demineralized water in order to form a slurry at a concentration of about 8% calculated on dry substance. The resulting slurry has a relative density of 1.032 kg/l compared to water. The pH of the modified starch slurry is adjusted to 6.0. The slurry is the heated to 160° C. by direct steam injection (Schlick Model 825). The temperature variation is not higher than ±1° C. The slurry is held in a holding column for a period of 4 minutes at a temperature of 160° C. and a pressure of about 5.5 bar. The pressure is then reduced to atmospheric by passing through a flash. The slurry is then contained at 95° C. in a hold tank.

D. Spray-Drying

The slurry from Part C is carried out using a Niro FSD 4 spray-drying tower equipped with a 0.8 mm nozzle and fed at 10 l/hour. The inlet temperature is fixed at 300° C. and the outlet temperature of 120° C. The obtained powder is a controlled release excipient with the following properties:

| Properties | |
|---|---|
| Moisture Content | 5.2% |
| Bulk Density | 103 g/l |
| Packed Density | 155 g/l |
| pH | 5.3 |
| Particle Size Peak Value (Laser Particle Sizer-Sympatec) | 70 μm |

Lubritab® is a product sold by Penwest Pharmaceuticals Co. (Cedar Rapids, Iowa, USA). Kollidon™ SR is a product produced by BASF (Germany). Encompress™ is a dicalcium phosphate dihydrate which can be purchased from Mendell (Patterson, N.Y.). Tramadol hydrochloride can be obtained from Chemagis Ltd., 3 Hashlosha Street, P.O. Box 9091, 61090, Tel Aviv, Israel. Methods of synthesis and purification of tramadol are described in, for example, U.S. Pat. Nos., 3,652,589, 5,414,129, 5,672,755, 5,874,620, 5,877,351, and 6,169,205.

Manufacturing Procedure

Tablets of the invention can be manufactured according to the process set out generally in the flow chart of FIG. 1, and described in more detail below.

Weighing:

Raw materials are dispensed into clearly labeled containers.

Core Pre-Blend:

Blend a portion of the Contramid® and Colloidal Silicon Dioxide and pass through #30 mesh screen into a suitable container.

Core Blend:

Place a portion of the Contramid® into a blender. Pass Tramadol Hydrochloride through a #30 mesh screen and add to blender. Rinse container with a portion of Contramid® and add to blender. Sieve Hydrogenated Vegetable Oil Type I through a #30 mesh screen and add to the blender. Add the Core Pre-Blend into the blender. Add the remaining Contramid® into the blender, and blend all ingredients. Sieve the Magnesium Stearate through a # mesh screen and add blend with other ingredients. Dispense blend in suitable container and identify as Core Blend.

Dry Coated Pre-Blend:

Blend a portion of the Xanthan Gum and all of the Colloidal Silicon Dioxide and pass through #30 mesh screen.

Dry Coated Blend:

Place a portion of the Kollidon® SR into a blender. Pass Tramadol Hydrochloride through Kason Separator with a #30 mesh screen into suitable container and add to blender. Rinse container with remaining xanthan gum and add to blender. Sieve Hydrogenated Vegetable Oil Type 1 through a #30 mesh screen and add to the blender Place Dry Coated Pre-Blend and the remainder of the Kollidon® SR into the blender, and blend with all ingredients. Sieve the magnesium stearate through a #30 mesh screen and blend with other ingredients. Dispense granulation in suitable container and identify as Dry Coated Blend.

Compression:

Use a Manesty Dry-Cota press to produce compression-coated tablets.

Example 1

Formulations A, B, and C, as shown in Table 3, were manufactured according to the process set out above.

TABLE 3

Recipes for Controlled Released Tramadol Formulations A, B and C

| Core | Formulation A | | Formulation B | | Formulation C | |
|---|---|---|---|---|---|---|
| | % | mg/tablet | % | mg/tablet | % | mg/tablet |
| 1) INGREDIENT | | | | | | |
| Tramadol Hydrochloride | 50 | 45 | 50 | 90 | 63.25 | 151.8 |
| Contramid ® | 48.3 | 43.47 | 48.3 | 86.94 | 35.05 | 84.1 |
| Hydrogenated Vegetable Oil | 0.75 | 0.675 | 0.75 | 1.35 | 0.75 | 1.8 |
| Silica | 0.2 | 0.18 | 0.2 | 0.36 | 0.20 | 0.5 |
| Magnesium Stearate | 0.75 | 0.675 | 0.75 | 1.35 | 0.75 | 1.8 |
| Core Total Weight | 100 | 90 | 100 | 180 | 100 | 240 |
| 2) COAT | | | | | | |
| Tramadol Hydrochloride | 21.15 | 55 | 30.56 | 110 | 30.56 | 148.5 |
| Silica | 0.20 | 0.52 | 0.20 | 0.72 | 0.20 | 1.0 |
| Kollidon SR ® | 51.42 | 133.7 | 45.16 | 162.58 | 45.16 | 219 |
| Xanthan Gum | 25.72 | 66.86 | 22.58 | 81.3 | 22.58 | 109.5 |
| Hydrogenated Vegetable Oil | 1.00 | 2.6 | 1.00 | 3.6 | 1.00 | 4.9 |
| Magnesium Stearate | 0.50 | 1.3 | 0.50 | 1.8 | 0.50 | 2.4 |
| Coat Total Weight | 100 | 260 | 100.00 | 360 | 100 | 485 |
| 3) COATED TABLET | | | | | | |
| Tramadol Hydrochloride | 28.57 | 100 | 37.04 | 200 | 41.38 | 300 |
| Contramid ® | 12.42 | 43.47 | 16.10 | 86.94 | 11.60 | 84.1 |
| Hydrogenated Vegetable Oil | 0.94 | 3.275 | 0.92 | 4.95 | 0.92 | 6.7 |
| Silica | 0.20 | 0.7 | 0.20 | 1.08 | 0.20 | 1.5 |
| Magnesium Stearate | 0.56 | 1.975 | 0.58 | 3.15 | 0.58 | 4.2 |
| Kollidon SR ® | 38.20 | 133.7 | 30.11 | 162.58 | 30.21 | 219 |
| Xanthan Gum | 19.11 | 66.86 | 15.06 | 81.3 | 15.10 | 109.5 |
| Coated Tablet Total Weight: | 100 | 350 | 100 | 540 | 100 | 725 |

Figure 2:
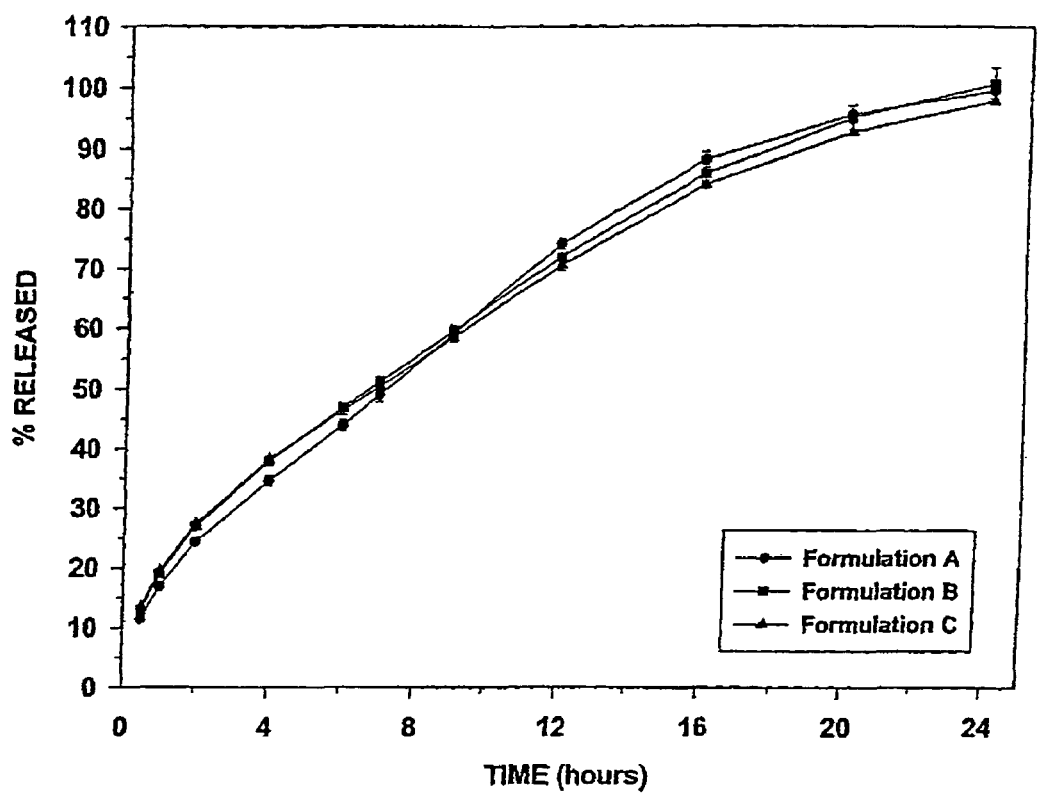
FIG. 2: Dissolution profiles (% released) of formulations A, B and C over 24 hours: In vitro performance of formulations A, B and C: under USP Type 1 Conditions; sodium phosphate buffer, 50 mM, pH 6.8, 100 rpm. 6 tablets were tested per time point.

Dissolution profiles of formulations A, B and C are shown in FIG. 2.

Bioavailability

Single Administration

Example 2

Figure 3A:
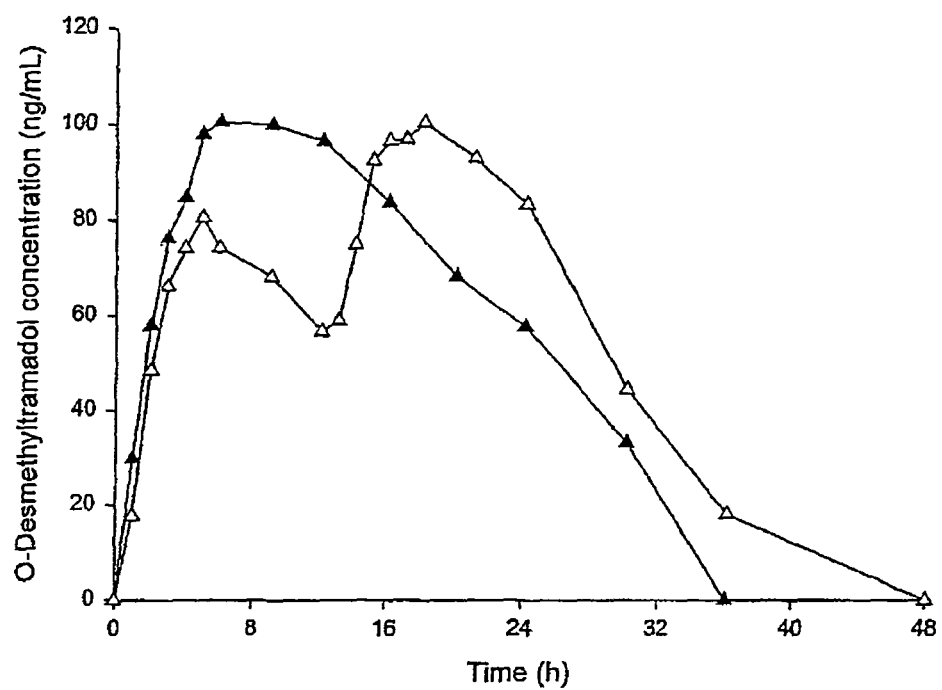
FIG. 3(a): Mean tramadol plasma concentrations (ng/ml) for 48 hours following administration of 2×200 mg doses of composition (formulation B) (▲), and 1×200 mg Topalgic® LP BID q12 h (Δ). Plasma concentrations were determined using an HPLC/UV assay.
Figure 3B:
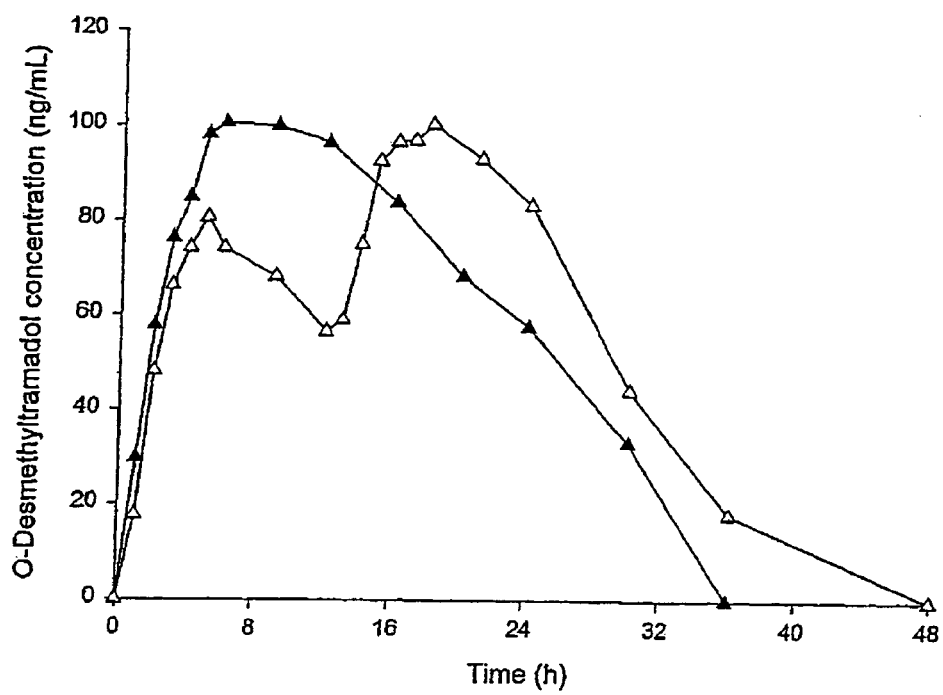
FIG. 3(b): Mean O-desmethyltramadol plasma concentrations (ng/ml) for 48 hours following a single administration of 1×200 mg dose of the composition (formulation B) (●), 2×200 mg dose of the composition (▲), 1×100 mg Topalgic® LP BID q12 h (○), and 1×200 mg Topalgic® LP BID q12 h (Δ).

The plasma pharmacokinetic profile of tramadol and its principal metabolite, O-desmethyltramadol, after a single oral administration of 200 mg, (formulation B) was determined in comparison to a currently available 100 mg formulation, Topalgic° administered two times a day, and after a double dose administration of 200 mg, (formulation B) was determined in comparison to a currently available 200 mg formulation, Topalgic® administered two times a day. The study was an open, single dose, randomized, three-way crossover design with at least a 7 day wash-out period between each administration. Results are shown in FIGS. 3(a) and 3(b).

Example 3

Figure 4A:
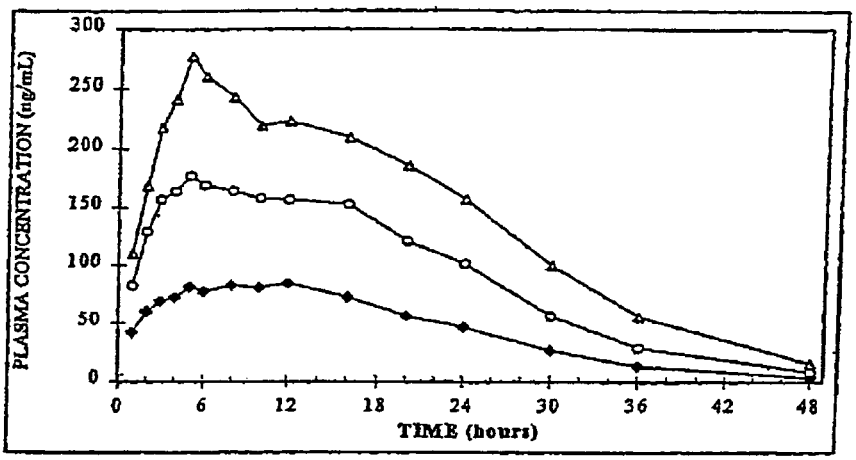
FIG. 4(a): Plasma tramadol concentrations (ng/ml) of 27 subjects for 48 hours following a single administration of either 100 mg (♦), 200 mg (○), or 300 mg (Δ) strength tramadol formulations (A, B, and C, respectively).
Figure 4B:
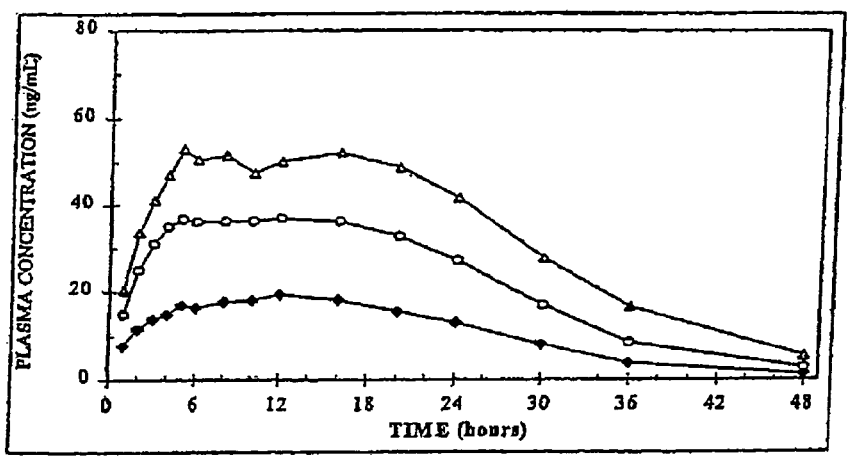
FIG. 4(b): Plasma O-desmethyl tramadol concentrations (ng/ml) of 27 subjects for 48 hours following a single administration of either 100 mg (♦), 200 mg (○), and 300 mg (Δ) strength tramadol formulations (A, B, and C, respectively).

The plasma pharmacokinetic profile of tramadol and its principal metabolite, O-desmethyltramadol, after a single oral administration of 100, 200 and 300 mg, formulations A, B and C, respectively, was determined. The study was an open, single dose, randomized, three-way cross-over design with at least a 7 day wash-out period between each administration. Results are shown in FIGS. 4(a) and 4(b).

A median time to tramadol peak plasma concentration ($T_{max}$) of between 2 and 8 hours and a mean peak tramadol plasma concentration ($C_{max}$) which is less than three times the mean plasma concentration obtained 24 hours after administration ($C_{24h}$) of a single dose of the composition was obtained. In a narrower sense, the peak tramadol plasma concentration ($C_{max}$) obtained in each case is less than two times the plasma concentration obtained 24 hours after administration ($C_{24h}$) of a single dose of a composition of the invention.

Example 4

Steady-State

Figure 5:
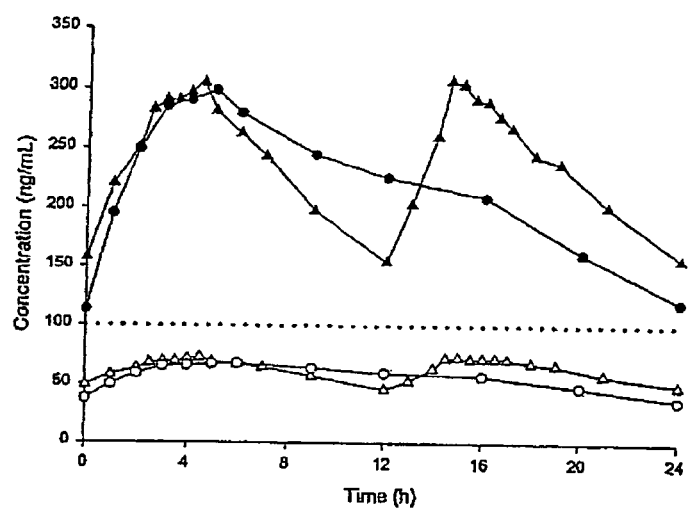
FIG. 5: Mean steady-state plasma tramadol (■) and O-desmethyl tramadol (○) concentrations (ng/ml) of 26 subjects dosed with the 200 mg tramadol, formulation B, and steady-state plasma tramadol (▲) and O-desmethyl tramadol (Δ) concentrations of 26 subjects dosed with Topalgic LP 100 mg BID.

The steady state plasma pharmacokinetic profile of tramadol and its principal metabolite, O-desmethyltramadol, following daily administration of 200 mg, formulation B, was determined. The profile was obtained in an open-label, two-period crossover randomized study. Results obtained are shown in FIG. 5.

The invention provides an oral tramadol pharmaceutical composition suitable for successive administration, once daily, comprising an effective amount of tramadol in vivo in a steady state in which, during a given 24 hour period, a tramadol maximum plasma concentration ($C_{max}$) of between 2 and 3 times a tramadol minimum plasma concentration ($C_{min}$) is obtained. More particularly, an average $C_{max}$ of no greater than 350 ng/ml is achievable. Further, a plasma concentration of tramadol of less than 90 percent of $C_{max}$ for at least 18 hours of the 24 hour period can be achieved, on average.

The term "$\lambda_z$" is the apparent terminal elimination rate constant, determined by the slope of the regression during the log-linear phase.

The term "$AUC_{0-Tmax}$" is the mean area under the plasma concentration-time curve from time 0 to Tmax and is used as an indicator of the rate of drug absorption, or metabolite formation. It is calculated as the arithmetic mean of the area under the plasma concentration-time curve from time 0 to $T_{max}$ calculated for each individual participating in the bioavailability study.

The term "$AUC_{0-\infty}$" is the mean area under the plasma concentration-time curve extrapolated to infinity. It is calculated as the arithmetic mean of the area under the plasma concentration-time curve from time 0 extrapolated to infinity, for each individual participating in the bioavailability study.

The term "$C'_{max}$" is the maximum observed plasma concentration, calculated as the mean of the individual maximum blood plasma concentrations.

The term "half-life" is the apparent terminal elimination half-life.

The term "HVD" is the half value duration, that is, the time during which tramadol concentrations are above one half the $C'_{max}$. This parameter is an indicator of the shape of the plasma concentration time curve, that is, the larger the value of HVD, the better the controlled release.

The term "MRT" is the mean residence time, which is an estimate of the average time that a tramadol molecule resides in the body following oral administration The term "$t_{max}$" is the time at which $C_{max}$ is achieved.

The term "$T_{max}$" is the time at which the maximum blood plasma concentration is observed for each individual participating in the bioavailability study.

The term "Rstart" is the time at which plasma concentrations begin to decline in a log-linear fashion, that is, the time at which either drug absorption or metabolite formation is complete Tramadol pharmacokinetic parameters of the controlled release composition are presented in Table 4, and O-desmethyltramadol pharmacokinetic parameters of the controlled release composition are presented in Table 5

TABLE 4

Summary of Tramadol Pharmacokinetic Parameters

| Formulation Strength (mg) | Dose (mg) | Descriptive Statistic | $C'_{max}$ (ng/mL) | $AUC_{0-\infty}$ (ng·h/mL) | $AUC_{0-Tmax}$ (ng·h/mL) | $C'_{max}/AUC_{0-\infty}$ (h$^{-1}$) | $\lambda_z$ (h$^{-1}$) | Restart (h) | half-life (h) | MRT (h) | HVD (h) | $AUC_{0-24}$ (ng·h/mL) | $AUC_{0-24}/AUC_{0-\infty}$ (%) |
|---|---|---|---|---|---|---|---|---|---|---|---|---|---|
| 100 | 100 | Arith. mean | 91.03 | 2108 | 625 | 0.0442 | 0.118 | 21.2 | 6.11 | 16.03 | 22.5 | 1635 | 78.9 |
|  |  | SD | 26.83 | 731 | 471 | 0.0052 | 0.024 | 4.3 | 1.31 | 2.13 | 3.4 | 465 | 6.60 |
| 200 | 200 | Arith. mean | 196.55 | 4416 | 915 | 0.0455 | 0.118 | 22.9 | 6.11 | 16.46 | 23.5 | 3374 | 77.2 |
|  |  | SD | 58.33 | 1192 | 567 | 0.0108 | 0.025 | 5.0 | 1.26 | 2.28 | 4.5 | 860 | 8.1 |
| 300 | 300 | Arith. mean | 290.08 | 6741 | 1578 | 0.0432 | 0.115 | 24.8 | 6.30 | 17.6 | 25.4 | 4900 | 73.9 |
| 300 | 300 | Arith. mean | 290.08 | 6741 | 1578 | 0.0432 | 0.115 | 24.8 | 6.30 | 17.60 | 25.4 | 4900 | 73.9 |
|  |  | SD | 147.16 | 2156 | 1338 | 0.0126 | 0.023 | 4.4 | 1.52 | 3.03 | 6.6 | 1544 | 10.1 |

NC—Not calculated

TABLE 5

Summary of O-desmethyltramadol Pharmacokinetic Parameters

| Formulation Strength (mg) | Dose (mg) | Descriptive Statistic | $C'_{max}$ (ng/mL) | $AUC_{0-\infty}$ (ng·h/mL) | $AUC_{0-Tmax}$ (ng·h/mL) | $C'_{max}/AUC_{0-\infty}$ (h$^{-1}$) | $\lambda_z$ (h$^{-1}$) | Restart (h) | half-life (h) | HVD (h) | $AUC_{0-24}$ (ng·h/mL) | $AUC_{0-24}/AUC_{0-\infty}$ (%) |
|---|---|---|---|---|---|---|---|---|---|---|---|---|
| 100 | 100 | Arith. mean | 20.38 | 520 | 179 | 0.0394 | 0.106 | 23.1 | 6.96 | 25.6 | 380 | 72.5 |
|  |  | SD | 6.67 | 170 | 92 | 0.0054 | 0.256 | 4.2 | 1.91 | 2.9 | 123 | 7.69 |
| 200 | 200 | Arith. mean | 43.13 | 1080 | 540 | 0.0395 | 0.111 | 25.1 | 6.69 | 26.3 | 782 | 71.3 |
|  |  | SD | 16.53 | 328 | 164 | 0.0079 | 0.029 | 4.0 | 1.8 | 5.0 | 259 | 8.8 |
| 300 | 300 | Arith. mean | 59.88 | 1641 | 587 | 0.0374 | 0.10 | 25.8 | 7.36 | 28.1 | 1107 | 67.9 |
|  |  | SD | 19.19 | 538 | 312 | 0.0092 | 0.029 | 3.6 | 2.21 | 6.6 | 346 | 11.0 |
| 200 | 400 | Arith. mean | 114.34 | 2866 | NC | 0.0457 | 0.09 | 18.7 | 8.14 | NC | 1909 | 74.6 |
|  |  | SD | 46.39 | 773 | NC | 0.0147 | 0.028 | 5.5 | 2.98 | NC | 651 | 10.9 |

NC—Not calculated

The present invention is not limited in scope by the specific embodiments disclosed in these examples which are intended to illustrate the most preferred embodiments of the invention. Indeed, various modifications of the invention or other embodiments which are functionally equivalent to those shown and described herein will become apparent to those skilled in the art and are intended to be covered by the appended claims. Further, although various examples of combined elements of the invention have been described, it will also be understood that these are not intended to be exhaustive and features of one embodiment may be combined with those of another, and such other combinations are contemplated to be within the scope of the invention disclosed herein.

A number of references have been cited, the entire disclosures of which are incorporated herein by reference.

The invention claimed is:

1. A solid dosage formulation comprising:
   a core comprising tramadol dispersed in a first controlled-release matrix comprising cross-linked high amylose starch; and
   a compression coat formed over the core and comprising tramadol dispersed in a second controlled-release matrix comprising a mixture of polyvinyl acetate and polyvinylpyrrolidone at a weight ratio of about 8:2 such that the mixture comprises from about 30% to about 65% by weight of the coat, wherein the initial rate of release of tramadol from the second controlled-release matrix is at least twice the initial rate of release of tramadol from the first controlled release matrix when measured separately for each matrix material in a USP Type I apparatus in 50 mM phosphate, pH 6.8, and stirring between 50 and 150 rpm.

2. The formulation of claim 1, wherein the tramadol is present in the formulation as an ionic salt.

3. The formulation of claim 1, wherein the rate of release of tramadol from the second controlled-release matrix is between three and nine times the rate of release of tramadol from the first controlled-release matrix.

4. The formulation of claim 1, wherein the rate of release of tramadol from the second controlled-release matrix is at least three times the rate of release of tramadol from the first controlled-release matrix.

5. The formulation of claim 1, wherein between 10% and 30% of tramadol present at 0 hours is released between 0 and 2 hours when tested in vitro using a USP Type I apparatus in 50 mM phosphate, pH 6.8, and stirring between 50 and 150 rpm.

6. The formulation of claim 1, wherein between 10% and 40% of the tramadol is released from the formulation between 0 and about 2 hours, between about 30% and 60% of the tramadol is released from the formulation between 2 and about 7 hours, between about 50% and 80% of the tramadol is released from the formulation between 7 and about 12 hours, and between about 80% and 100% of the tramadol is released from the formulation after about 20 hours.

7. The formulation of claim 1, wherein the ratio of the core to the coat (w/w) is between about 1 and about 0.1.

8. The formulation of claim 1, wherein the ratio of the tramadol in the core to the tramadol in the coat (w/w) is between about 0.6 and about 2.

9. The formulation of claim 1, wherein the coat is between about 5% and about 90% by weight tramadol.

10. The formulation of claim 1, wherein the ratio of the matrix of the coat to the tramadol of the coat (w/w) is between about 0.7 and about 4.

11. The formulation of claim 1, wherein the ratio of the matrix of the core to the tramadol of the core (w/w) is between about 0.1 and about 10.

12. The formulation of claim 1, wherein the coat further comprises a binding agent.

13. The formulation of claim 12, wherein the binding agent is xanthan gum.

14. The formulation of claim 1, wherein the formulation is a tablet, and wherein the cross-linked high amylose starch comprises a chemically-modified, cross-linked high amylose starch prepared by a method comprising:
   (a) cross-linking high amylose starch, followed by
   (b) chemically modifying the cross-linked high amylose starch by hydroxypropylating the cross-linked high amylose starch, followed by
   (c) gelatinization, and
   (d) drying to obtain a powder of the controlled release excipient;
   wherein the cross-linked high amylose starch is characterized in that upon solubilization in 90% DMSO at 80° C. for about three days and gel permeation chromatography, the height of the peak corresponding to amylose in the cross-linked high amylose starch is at least 90% of that of the peak corresponding to amylose in the high amylose starch prior to (a).

15. The formulation of claim 1, wherein the core further comprises a lubricant.

16. The formulation of claim 1, wherein the coat further comprises a lubricant.

17. The formulation of claim 1, wherein the formulation is a tablet formulated for oral administration.

18. A controlled released tablet comprising:
   a compressed core comprising cross-linked high amylose starch and tramadol, or a salt thereof; and
   a coat formed over the core by compression, and comprising a mixture of polyvinyl acetate, polyvinylpyrrolidone, a binder, and tramadol; and wherein:
   the ratio of the core/coat (w/w) is between about 0.2 and 0.6;
   the ratio of the tramadol in the core to the tramadol in the coat is between about 0.7 and about 1;
   the ratio of polyvinyl acetate/polyvinylpyrrolidone (w/w) is about 8:2; and
   the rate of release of tramadol from the coat is at least twice the rate of release of tramadol from the core when measured by a USP Type I apparatus in 50 mM phosphate, pH 6.8, and between 50 and 150 rpm.

19. A method of administering a pharmacological agent, the method comprising administering to a patient a solid dosage formulation as defined in claim 1 or 18.

20. The formulation of claim 18, wherein the polyvinyl acetate has a molecular weight in the range from about 100,000 to about 1,000,000.

21. The formulation of claim 18, wherein the polyvinylpyrrolidone has a molecular weight in the range from about 10,000 to about 100,000.

22. The formulation of claim 18, wherein the formulation is a once daily oral pharmaceutical composition for controlled release of tramadol or a salt thereof, wherein the composition, upon initial administration of one dose, provides a mean plasma concentration of at least 100 ng/mL within two hours of administration and continues to provide a mean plasma concentration of at least 100 ng/mL for at least 22 hours after administration.

23. The formulation of claim 22, wherein the maximum mean plasma concentration is less than 2.2 times the mean plasma concentration obtained 24 hours after administration.

* * * * *